(12) United States Patent
Reddy et al.

(10) Patent No.: US 10,300,071 B2
(45) Date of Patent: May 28, 2019

(54) COMPOSITIONS AND METHODS FOR INHIBITION OF MYCOBACTERIA

(71) Applicant: The Texas A&M University System, College Station, TX (US)

(72) Inventors: Manchi C M Reddy, College Station, TX (US); James C. Sacchettini, College Station, TX (US); Nian E. Zhou, Naperville, IL (US); Billy F. McCutchen, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 15/248,844

(22) Filed: Aug. 26, 2016

(65) Prior Publication Data
US 2017/0065601 A1  Mar. 9, 2017

Related U.S. Application Data

(63) Continuation of application No. PCT/US2015/017936, filed on Feb. 27, 2015.

(60) Provisional application No. 61/946,284, filed on Feb. 28, 2014.

(51) Int. Cl.
| | | |
|---|---|---|
| A61K 31/428 | (2006.01) |
| A61K 31/498 | (2006.01) |
| A61K 31/5377 | (2006.01) |
| A61K 31/423 | (2006.01) |
| A61K 31/44 | (2006.01) |
| A61K 31/4439 | (2006.01) |
| A61K 31/454 | (2006.01) |
| A61K 31/496 | (2006.01) |
| A61K 31/501 | (2006.01) |

(52) U.S. Cl.
CPC ........ *A61K 31/5377* (2013.01); *A61K 31/423* (2013.01); *A61K 31/428* (2013.01); *A61K 31/44* (2013.01); *A61K 31/4439* (2013.01); *A61K 31/454* (2013.01); *A61K 31/496* (2013.01); *A61K 31/498* (2013.01); *A61K 31/501* (2013.01)

(58) Field of Classification Search
CPC .......................... A61K 31/428; A61K 31/498
See application file for complete search history.

(56) References Cited

U.S. PATENT DOCUMENTS

| | | |
|---|---|---|
| H1401 H | 1/1995 | Campbell |
| 6,545,003 B1 | 4/2003 | Grant et al. |
| 2006/0047171 A1 | 3/2006 | Meckler et al. |
| 2010/0029752 A1 | 2/2010 | Kuhajda et al. |
| 2010/0130737 A1 | 5/2010 | Itoh et al. |
| 2012/0101105 A1 | 4/2012 | Inoue et al. |

FOREIGN PATENT DOCUMENTS

| | | |
|---|---|---|
| EP | 0133034 | 4/1990 |
| WO | WO 88/04294 | * 7/1988 |
| WO | 2010/047774 | 4/2010 |
| WO | 2015/131019 | 9/2015 |

OTHER PUBLICATIONS

Pwealczyk et al. Journal of Bacteriology, 2011, vol. 193, No. 24, pp. 6960-6972.*
Piras et al. II Farmaco, 2004, vol. 59, pp. 185-194 (Year: 2004).*
Gande, Roland, et al. "The two carboxylases of Corynebacterium glutamicum essential for fatty acid and mycolic acid synthesis." Journal of bacteriology 189.14 (2007): 5257-5264; 8 pages.
Reddy, Manchi CM, et al. "Structure, activity, and inhibition of the Carboxyltransferase β-subunit of acetyl coenzyme A carboxylase (AccD6) from *Mycobacterium tuberculosis*." Antimicrobial agents and chemotherapy 58.10 (2014): 6122-6132; 11 pages.
Tomita, Masao et al. "Structure, Activity, and Inhibition of the Caiboxyltransferase—Subunit of Acetyl Coenzyme A Carboxylase (AccD6) from *Mycobacterium tuberculosis*", Antimicrobial Agents and Chemotherapy, vol. 58, No. 10, Oct. 1, 2014, pp. 6122-6132, XP055325669, ISSN: 0066-4804, DOI: 10.1128/AAC.02574-13; 3 pages.
Database CA [Online] Chemical Abstracts Service, Columbus, Ohio, US; "(R)-4-Substituted-.alpha.-phenoxypropionic acids", retrieved from STN Database accession No. 1985:613403; & "(R)-4-Substituted-.alpha.-phenoxypropionic acids", Jpn. Kokai Tokkyo Koho, 3 pp. CODEN: JKXXAF; 2 pages, Jun. 13, 2017.
Partial Supplementary European Search Report received for European Patent Application No. 15756011.1, dated Aug. 7, 2017; 18 pages.
Database CA [Online] Chemical Abstracts Service, Columbus, Ohio, US; Nishizawa, Kanji et al. "Optically active 1-(4-phenoxyphenoxy)propan-2-ol by enzymic hydrolysis of its esters", retrieved from STN Database accession No. 1986:607608; & Nishizawa, Kanji et al. "Optically active 1-(4-phenoxyphenoxy)propan-2-ol by enzymic hydrolysis of its esters", Jpn. Kokai Tkkyo Koho, 10 pp. CODEN: JKXXAF; 3 pages.
International Preliminary Report on Patentability of PCT Application No. PCT/US2015/017936, dated Sep. 15, 2016; 6 pages.
International Search Report and Written Opinion of PCT Application No. PCT/US2015/017936, dated May 27, 2015; 10 pages.
Harris, DM et al. Exploring and dissecting genome-wide gene expression reasponses of Penicillium chrysogenum to phenylacetic acid consumption and penicillinG production, BMC Genomics. vol. 10, Feb. 10, 2009, 75 pp. 1-20 [online], [retrieved on Apr. 27, 2015]. Retrieved from the Internet <URL:http://www.ncbi.nlm.nih.gov/pmc/articles/PMC2657799/><doi:10.1186/1471-2164-10-75>; abstract.

(Continued)

*Primary Examiner* — James D. Anderson
(74) *Attorney, Agent, or Firm* — Baker Botts L.L.P.

(57) ABSTRACT

A composition comprising a drug selected from the group consisting of an arylphenoxypropionate derivative, an aryloxyphenoxyacetate derivative, an aryloxyphenylacetate derivative, a substituted quinol, or a salt, hydrate, or prodrugs thereof, or a combination thereof, in an amount and formulation sufficient to inhibit a *mycobacterium* is disclosed.

18 Claims, 9 Drawing Sheets
(3 of 9 Drawing Sheet(s) Filed in Color)
Specification includes a Sequence Listing.

(56) References Cited

OTHER PUBLICATIONS

Daniel, J et al. AccD6, a Member of the Fas II Locus, Is a Functional Carboxyltransferase Subunit of the Acyl-Coenzyme A Carboxylase in *Mycobacterium tuberculosis*. Journal of Bacteriology, vol. 189, No. 3, Feb. 3, 2009, pp. 911-917. Epublished Nov. 17, 2006 [online], [retrieved on Apr. 27, 2015]. Retrieved from the Internet <URL: http:jb.asm.org/content/189/3/911.full.pdf+html>; abstract; p. 914, col. 1, paragraph 3.

\* cited by examiner

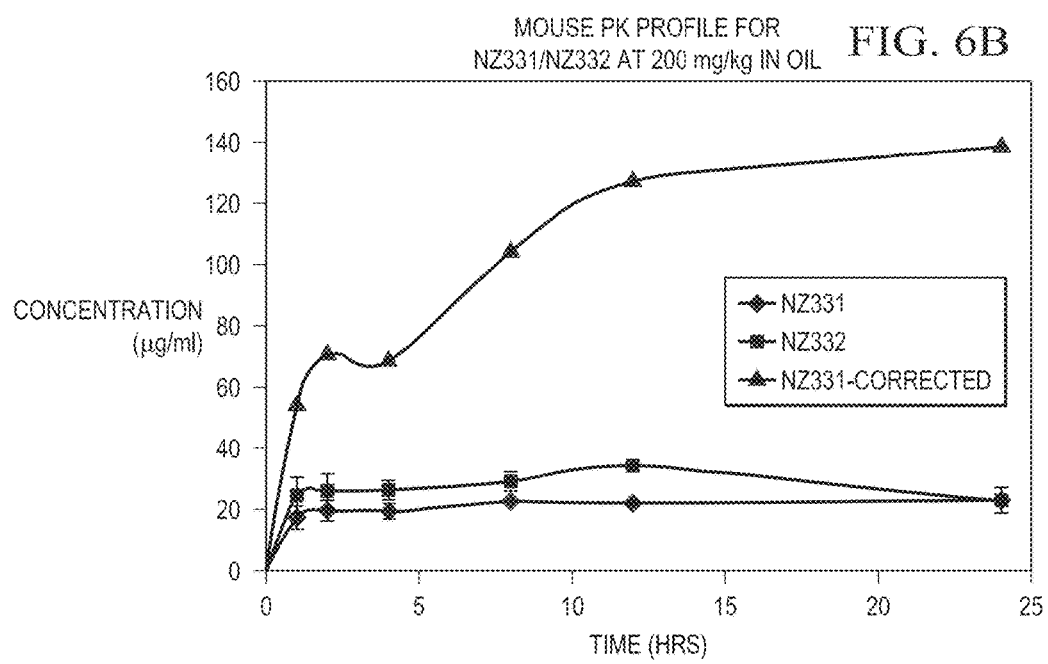
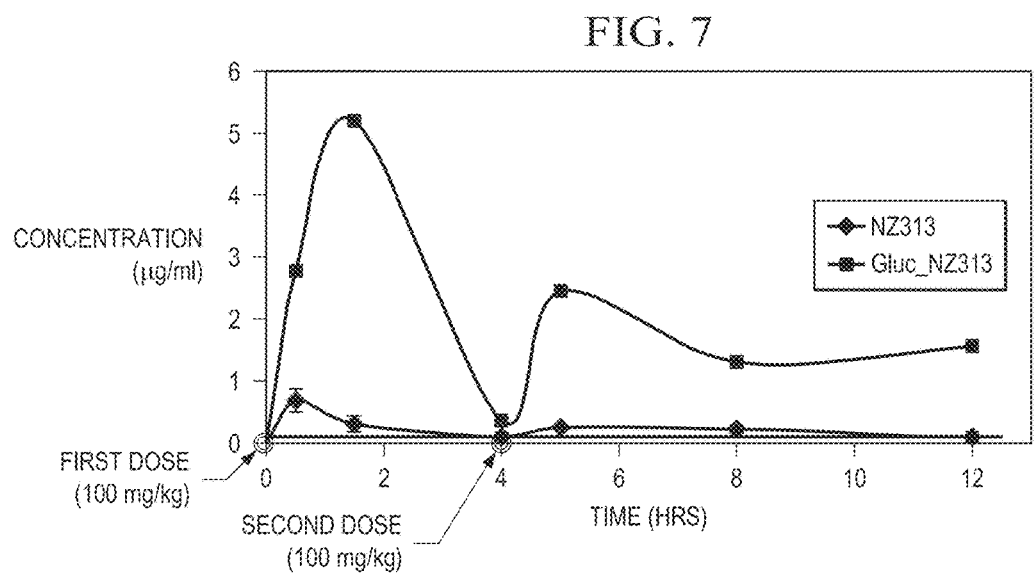

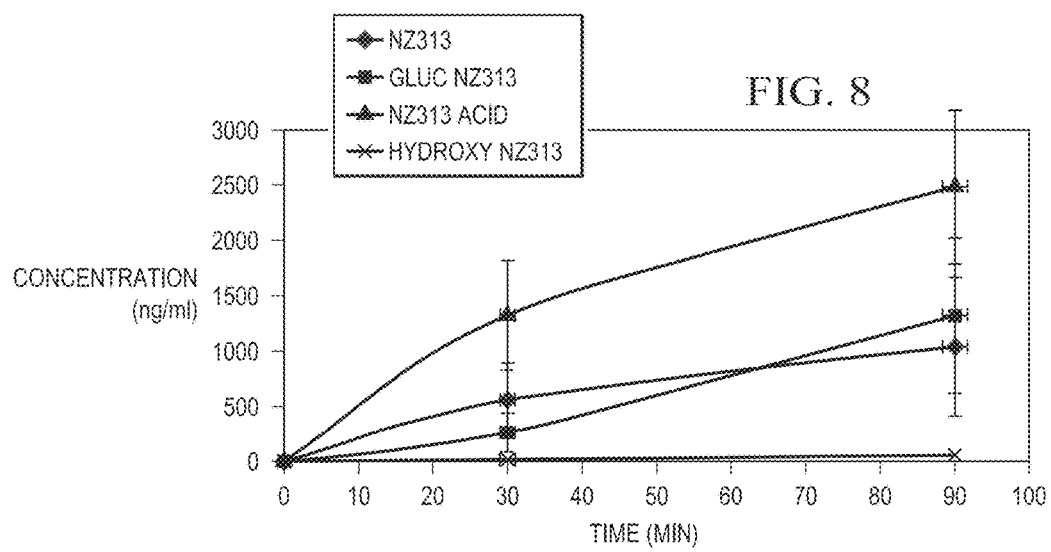
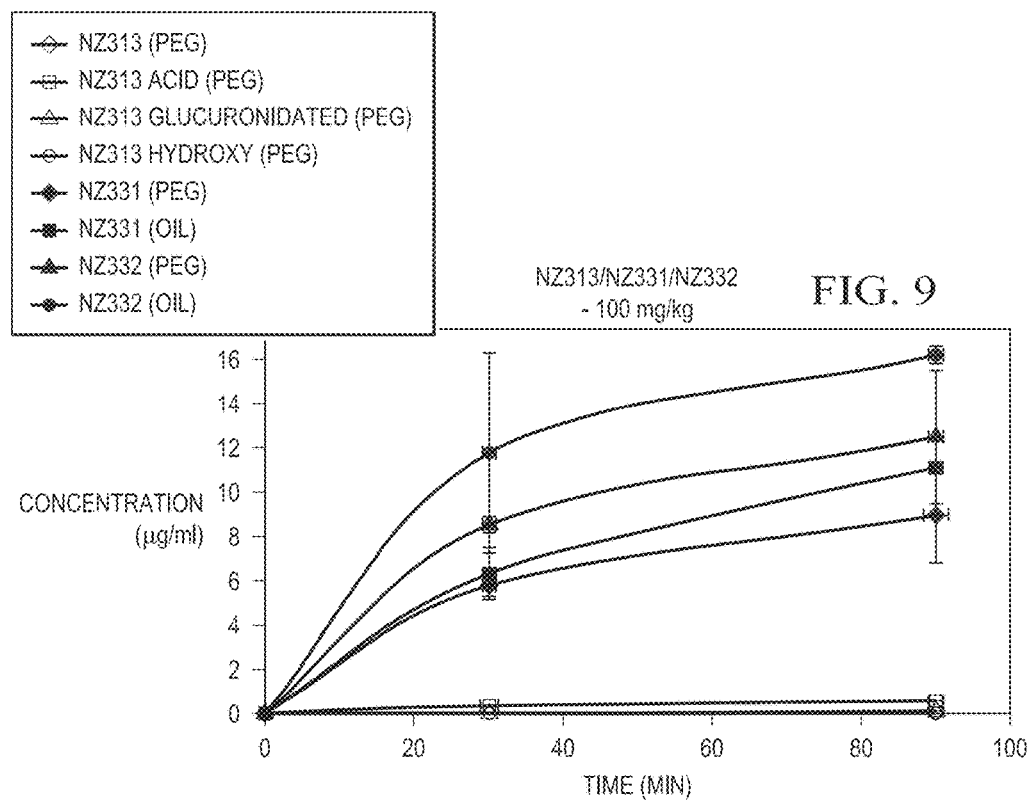

COMPOSITIONS AND METHODS FOR INHIBITION OF MYCOBACTERIA

CROSS-REFERENCE TO RELATED APPLICATION

The present application is a continuation application of PCT International Application Number PCT/US2015/017936 filed Feb. 27, 2015, which claims priority to U.S. Provisional Application No. 61/946,284 filed Feb. 28, 2014, the contents of which are hereby incorporated by reference in their entirety for all purposes.

TECHNICAL FIELD

Reference to Sequence Listing Submitted Via EFS-Web

This application includes an electronically submitted sequence listing in .txt format. The .txt file contains a sequence listing entitled "2016-11-10 017575.1572 ST25.txt" created on Nov. 10, 2016 and is 652 bytes in size. The sequence listing contained in this .txt file is part of the specification and is hereby incorporated by reference herein in its entirety.

The present disclosure relates to compositions for inhibition of Mycobacterium, including, but not limited to, Mycobacterium tuberculosis. In particular, the present disclosure relates to compositions including one or more arylphenoxypropionate derivatives, such as, but not limited to, quizalofop, fenoxaprop, proquizalofop, and haloxyfop, one or more aryloxyphenoxyacetate derivatives, one or more aryloxyphenylacetate derivatives, and one or more substituted quinols. The present disclosure also relates to methods of inhibiting a Mycobacterium bacterium using one or more arylphenoxypropionate derivatives, one or more aryloxyphenoxyacetate derivatives, one or more aryloxyphenylacetate derivatives, and one or more substituted quinols.

BACKGROUND

Tuberculosis

Tuberculosis is a common, chronic, and frequently fatal infectious disease caused by various strains of mycobacteria, most commonly Mycobacterium tuberculosis. Drug-resistance and multi-drug resistance in tuberculosis is increasing, diminishing the efficacy of first- and second-line tuberculosis drugs. Drugs used for the treatment of tuberculosis involve the combination of multiple agents such as isoniazid, rifampicin, pyrazinamide, ethambutol, streptomycin, para-amino salicylic acid, ethionamide, cycloserine, capreomycin, kanamycin, ciprofloxacin, ofloxacin, thioacetazone, Rifapentine, Bedaquiline, and Rifampin. The regimen recommended by the US Public Health Service (http://www.hhs.gov/pharmacy/pp/DHHSpresent/) is a combination of isoniazid, rifampicin, and pyrazinamide for two months, followed by isoniazid and rifampicin, together, for another four months. These drugs are continued for another seven months in patients infected with HIV. For the treatment of multi-drug resistant tuberculosis, streptomycin, kanamycin, amikacin, capreomycin, ethionamide, cycloserine, ciprofloxacin, and ofloxacin are added to the combination therapies (World Health Organization, Anti-tuberculosis drug resistance in the world Third Global Report 2004). Currently, there is neither a single agent nor a combination therapy that can both treat tuberculosis and shorten the duration of treatment. All existing approaches to tuberculosis treatment involve the combination of multiple agents. No single agent exists that is effective in the clinical treatment of tuberculosis, nor is there any combination of agents that offer the possibility of a therapeutic regimen having less than a six month duration. An urgent need exists for novel and potent inhibitors of pathogenic mycobacteria.

Mycobacterium tuberculosis (Mtb) is characterized by an unusually lipid-rich cell wall of low permeability which allows the bacterium to survive in the hostile environment of the macrophage and cause infection. Mycobacterial lipids are essential for both viability and pathogenicity.

The first step of fatty-acid biosynthesis is mediated by acyl-CoA carboxylase (ACC). ACC catalyzes the carboxylation reaction of acetyl-CoA to produce malonyl-CoA, a precursor in long chain fatty acid biosynthesis. These fatty acids are essential for survival, virulence, and antibiotic resistance in Mtb. In particular, the D6 carboxyltransferase β-subunit (AccD6) has been shown to be essential to pathogenic mycobacteria, indicating that this enzyme represents an ideal target for inhibition. The AccD6 gene in M. bovis shares complete sequence identity with that of Mtb.

Most bacteria have a multi-subunit ACC composed of three functional polypeptides: BC (AccC), BCCP (AccB), and CT (AccA plus AccD) (2). For example, in *Escherichia coli* and *Staphylococcus aureus*, these Accs are composed of three independent (BC, BCCP, and CT) functional proteins (2). In yeast and mammals, these functions are carried out by a single polypeptide with distinct BC, BCCP, and CT domains (3). In comparison, the Mtb genome contains three BC α-subunits (AccA1 to Acc3) and six CT β-subunits (AccD1 to D6) (14). The high number of β-subunits is unusual as other bacteria generally only have 1-2 ACCases. The multiple β-subunits likely reflect the ability of mycobacteria to carboxylate other distinct substrates, including the short acyl CoAs used as intermediates in glycolipid biosynthesis. Therefore, the presence of multiple AccA and AccD genes contained within the Mtb genome is thought to be linked to the wide variety of lipids found in Mtb.

ACC Inhibitors

Arylphenoxypropionate derivatives are potent inhibitors of ACCs, and several arylphenoxypriopionate derivatives, including haloxyfop, are currently used in herbicides in light of their species-dependent ACC inhibition. Commercially available arylphenoxypropionate derivatives exhibit little human toxicity. Quizalofop-p-ethyl, for example, has $LD_{50}$ values of 1753 to 2350 mg/kg in male mice and 1805 to 2360 mg/kg in female mice. In rabbits, it was reported that $LD_{50}$ values were greater than 2,000 mg/kg. Also it was shown in a 1-year feeding study on dogs that doses of up to 10 mg/kg/day caused zero observed effects. This compound is rapidly broken down in mammals; more than 90% of a single oral dose is eliminated in urine within three days. The Carcinogenicity Peer Review Committee CPRC has classified quizalofop ethyl as a Group D carcinogen (i.e., not classifiable as to human cancer potential). To date, however, there are no bacterial ACC inhibitors in clinical use as antibiotics.

SUMMARY

The present disclosure, in certain embodiments, relates to compositions for inhibiting a *mycobacterium* comprising one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof. The compositions are operable to inhibit a pathogenic *mycobacterium*.

According to certain embodiments, the disclosure provides methods of inhibiting a *mycobacterium* by administering one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof to the *mycobacterium* in an amount and for a time sufficient to inhibit the *mycobacterium*.

According to certain embodiments, the disclosure provides methods of inhibiting a mycobacterial ACC by administering one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof, to the *mycobacterium* in an amount and for a time sufficient to inhibit the mycobacterial ACC.

According to certain embodiments, the disclosure provides methods of inhibiting a mycobacterial AccD6 by administering one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof, to the *mycobacterium* in an amount and for a time sufficient to inhibit the mycobacterial AccD6.

The following abbreviations are used throughout the specification:

Mtb—*Mycobacterium tuberculosis*
AccD6—Acetyl-CoA carboxyltransferase β-subunit D6

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A more complete understanding of the present embodiments and advantages thereof may be acquired by referring to the following description taken in conjunction with the accompanying drawings, which depict embodiments of the present disclosure, and in which like numbers refer to similar components, and in which:

FIG. 6B illustrates the corrected plasma concentration of NZ-331 in blood samples collected from mice following administration of two doses of NZ-331 and NZ-332 dissolved in canola oil by gavage at a dosage of 200 mg/kg.

FIG. 7 illustrates the plasma concentration of NZ-313 in blood samples collected from mice following administration of two doses of NZ-313 dissolved in canola oil by gavage at a dosage of 100 mg/kg.

FIG. 8 illustrates the plasma concentration of NZ-313 in blood samples collected from mice following administration of a single dose of NZ-313 dissolved in polyethylene glycol (PEG) by gavage at a dosage of 200 mg/kg.

FIG. 9 provides a comparison of the plasma concentration of NZ-313, NZ-313 acid, NZ-313 glucuronidated, NZ331, and NZ-332 in blood samples collected from mice following administration of a single dose of 100 mg/kg.

DETAILED DESCRIPTION

Figure 1A:
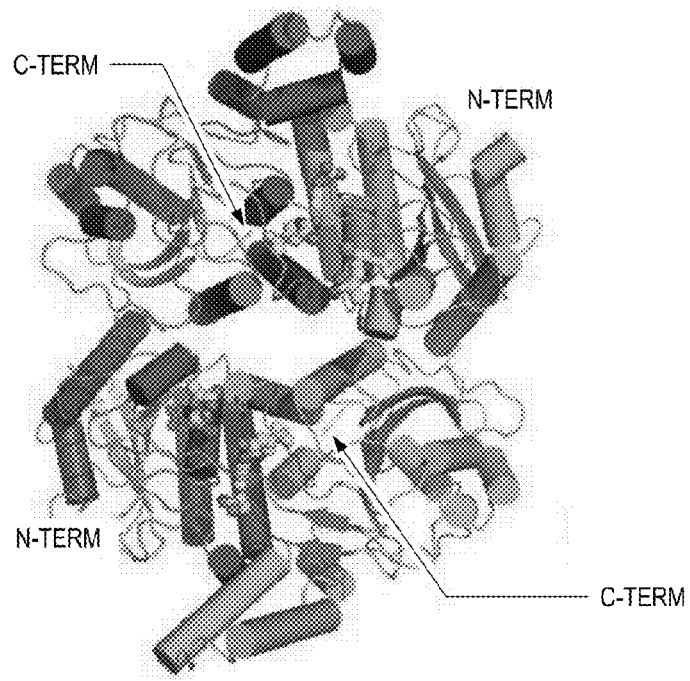
FIG. 1A illustrates schematically the crystal structure of the haloxyfop-bound Mtb holoenzyme.

The present disclosure relates to compositions and methods for inhibition of a *mycobacterium*. These compositions and methods are described in further detail below.

Unless otherwise indicated by the specific context of this specification, a *mycobacterium* may include any species of the genus *Mycobacterium*. Furthermore, it may include a *mycobacterium* in a patient. The patient may be any animal. In particular, the patient may be a mammal, such as a human, a pet mammal such as a dog or cat, an agricultural mammal, such as a horse, cow, buffalo, deer, pig, sheep, or goat, or a zoo mammal. Although many embodiments herein are expressed in terms of a single *mycobacterium*, the same or similar effects may be seen in groups of mycobacteria in a patient.

Mycobacterial inhibition, unless otherwise indicated by the specific context of this specification, can include killing the *mycobacterium*, such as via apoptosis or necrosis, reducing or arresting the growth of the *mycobacterium*, rendering the *mycobacterium* more susceptible to the immune system, preventing or reducing mycobacterial infection, reducing the number of mycobacteria in a patient, or otherwise negatively affecting a *mycobacterium*.

Compositions

The present disclosure includes antimycobacterial compositions including one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof.

In certain embodiments, the present disclosure provides arylphenoxypropionate derivatives according to one of the following structures:

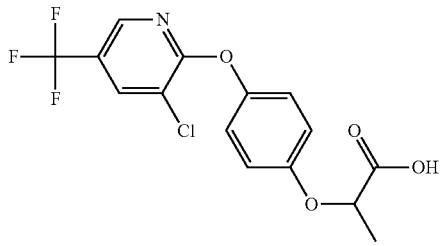 [SMILES: CC(Oc1ccc(Oc2ncc(C(F)(F)F)cc2Cl)cc1)C(=O)O]

haloxyfop (IUPAC name: (RS)-2-{4-[3-chloro-5-(trifluoromethyl)-2-pyridyloxy]phenoxy}propionic acid);

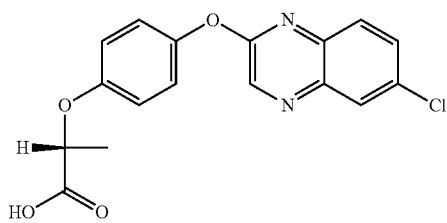 [SMILES: C[C@@H](Oc1ccc(Oc2cnc3cc(Cl)ccc3n2)cc1)C(=O)O]

quizalofop-p (IUPAC name: (R)-2-[4-(6-chloroquinoxalin-2-yloxy)phenoxy]propionic acid);

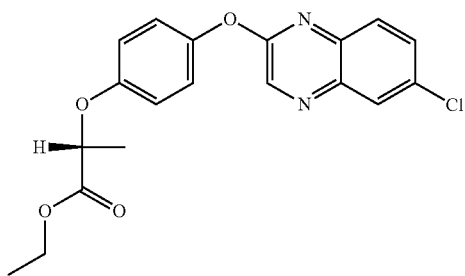 [SMILES: CCOC(=O)[C@@H](C)Oc1ccc(Oc2cnc3cc(Cl)ccc3n2)cc1]

quizalofop-p-ethyl (IUPAC name: ethyl (2R)-2-[4-(6-chloroquinoxalin-2-yloxy)phenoxy]propionate);

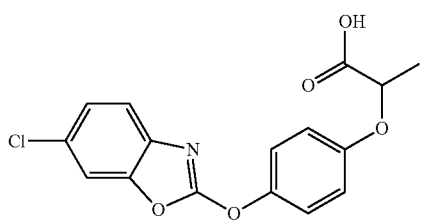 [SMILES: CC(Oc1ccc(Oc2nc3ccc(Cl)cc3o2)cc1)C(=O)O]

fenoxaprop-p (IUPAC name: (R)-2-[4-(6-chlorobenzoxazol-2-yloxy)phenoxy]propionic acid;

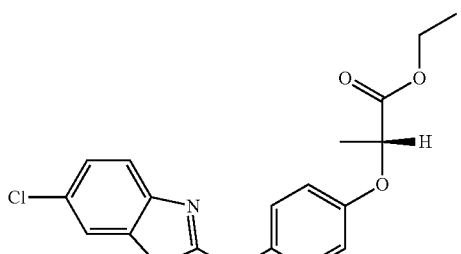

fenoxaprop-p-ethyl (IUPAC name: ethyl (R)-2-[4-(6-chlorobenzoxazol-2-yloxy)phenoxy]propionate); or

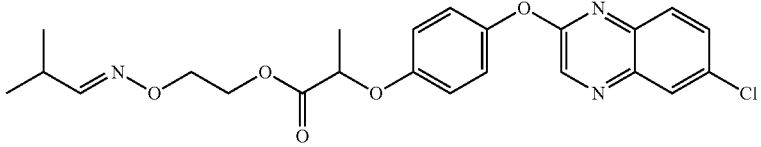 [SMILES: CC(C)/C=N/OCCOC(=O)C(C)Oc1ccc(Oc2cnc3cc(Cl)ccc3n2)cc1]

proquizafop (IUPAC name: 2-isopropylideneaminooxyethyl (R)-2-[4-(6-chloroquinoxalin-2-yloxy)phenoxy]propionate); and enantiomers of the general structures.

In certain embodiments, the present disclosure provides aryloxyphenoxyacetate derivatives according to the following structure:

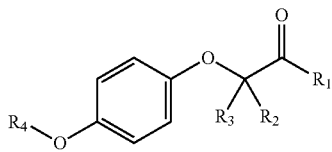

wherein $R_1$ is selected from —$OR_5$, —$NR_6R_7$ and —NH—$SO_2$—$R_8$ groups; $R_2$ and $R_3$ are independently selected from hydrogen, alkyl, alkenyl, alkynyl, cycloalkyl, aryl, and heteroaryl groups; or $R_2$ and $R_3$ together are a cycloalkyl group; $R_4$ is selected from the group consisting of aryl, heteroaryl, bicycloaryl, and bicycloheteroaryl groups optionally additionally substituted with from zero to four substitutions selected independently from halogen, hydroxyl, alkyl, alkoxy, nitril, nitro, amino, alkylamino, dialkylamino, dialkylaminoalkyl, carboxy, acyl, carboxamido, alkylsulfoxide, acylamino, phenyl, benzyl, phenoxy, and benzyloxy groups; R₅ is selected from hydrogen or an alkyl, aryl, or benzyl group that is optionally additionally substituted with an alkyloxy, alkylamino, dialkylamino, or acylamino group; R₆ and R₇ are independently selected from hydrogen, alkyl, alkenyl, alkynyl, cycloalkyl, heterocycloalkyl, aryl, heteroaryl, and alkoxy groups; or R₆ and R₇ together are a cycloalkyl or heterocycloalkyl group; and R₈ is an alkyl or aryl group optionally substituted with halogen.

In certain embodiments, the present disclosure provides aryloxyphenylacetate derivatives according to the following structure:

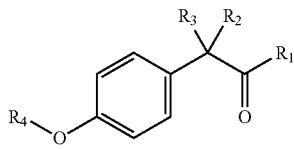

wherein R₁ is selected from —OR₅, —NR₆R₇ and —NH—SO₂—R₈ groups; R₂ and R₃ are independently selected from hydrogen, alkyl, alkenyl, alkynyl, cycloalkyl, aryl, and heteroaryl groups; or R₂ and R₃ together are a cycloalkyl group; R₄ is selected from the group consisting of aryl, heteroaryl, bicycloaryl, and bicycloheteroaryl groups optionally additionally substituted with from zero to four substitutions selected independently from halogen, hydroxyl, alkyl, alkoxy, nitril, nitro, amino, alkylamino, dialkylamino, dialkylaminoalkyl, carboxy, acyl, carboxamido, alkylsulfoxide, acylamino, phenyl, benzyl, phenoxy, and benzyloxy groups; R₅ is selected from hydrogen or an alkyl, aryl, or benzyl group that is optionally additionally substituted with an alkyloxy, alkylamino, dialkylamino, or acylamino group; R₆ and R₇ are independently selected from hydrogen, alkyl, alkenyl, alkynyl, cycloalkyl, heterocycloalkyl, aryl, heteroaryl, and alkoxy groups; or R₆ and R₇ together are a cycloalkyl or heterocycloalkyl group; and R₈ is an alkyl or aryl group optionally substituted with halogen.

In certain embodiments, the present disclosure provides substituted quinols according to the following structure:

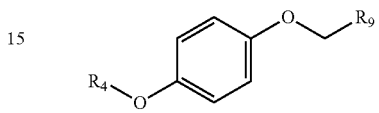

wherein R₉ is selected from nitril, hydroxyl, heterocycloaryl and alkyloxy groups; and R₄ is selected from the group consisting of aryl, heteroaryl, bicycloaryl, and bicycloheteroaryl groups optionally additionally substituted with from zero to four substitutions chosen independently from the group consisting of halogen, hydroxyl, alkyl, alkyloxy, nitril, nitro, amino, alkylamino, dialkylamino, dialkylaminoalkyl, carboxy, acyl, carboxamido, alkylsulfoxide, acylamino, phenyl, benzyl, phenoxy, and benzyloxy groups.

Specific compounds of the invention include those named in Table 1 and characterized in the examples herein.

TABLE 1

Arylphenoxypropionate Derivatives

| | | |
|---|---|---|
| WuXi-N8 | (structure) | 1-{5-[(6-chloro-1,3-benzothiazol-2-yl)oxy]pyridin-2-yl}-3-(propan-2-yl)urea |
| WuXi-N7 | (structure) | 1-{6-[(6-chloro-1,3-benzothiazol-2-yl)oxy]pyridazin-3-yl}-3-(propan-2-yl)urea |
| WuXi-N6 | (structure) | 1-{6-[(6-chloro-1,3-benzothiazol-2-yl)oxy]pyridin-3-yl}-3-(propan-2-yl)urea |
| WUXI-N5 | (structure) | 3-{4-[(6-chloro-1,3-benzothiazol-2-yl)oxy]piperidin-1-yl}-N-methoxypropanamide |
| WUXI-N4 | (structure) | 2-{4-[(6-chloro-1,3-benzothiazol-2-yl)oxy]piperidin-1-yl}-N-methoxyacetamide |

TABLE 1-continued
Arylphenoxypropionate Derivatives
| | | |
|---|---|---|
| quizalofop-p-ethyl | 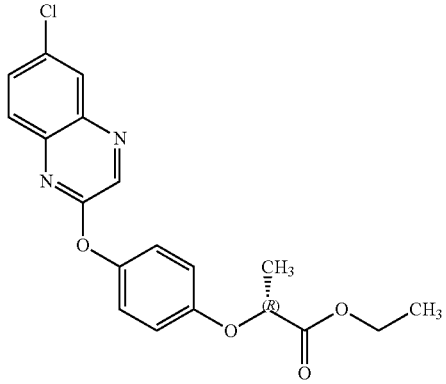 | ethyl (2R)-2-{4-[(6-chloroquinoxalin-2-yl)oxy]phenoxy}propanoate |
| quizalofop-p | 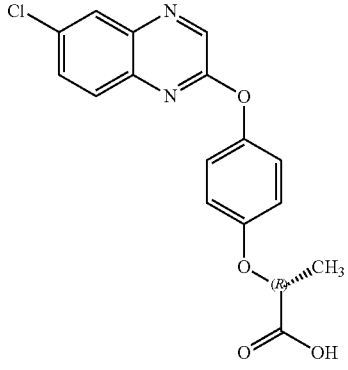 | (2R)-2-{4-[(6-chloroquinoxalin-2-yl)oxy]phenoxy}propanoic acid |
| propaquizafop | 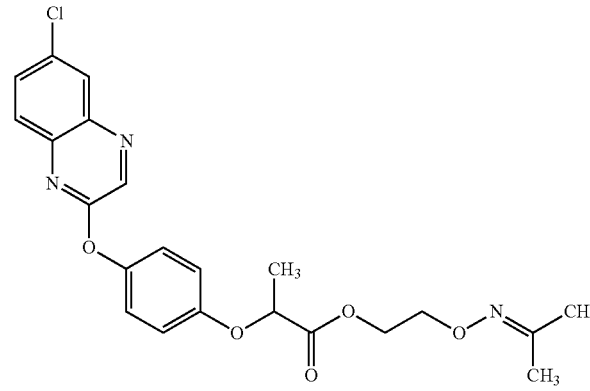 [SMILES: CC(C)=NOCCOC(=O)C(C)Oc1ccc(Oc2cnc3cc(Cl)ccc3n2)cc1] | 2-{[(propan-2-ylidene)amino]oxy}ethyl 2-{4-[(6-chloroquinoxalin-2-yl)oxy]phenoxy}propanoate |
| NZ-420 | 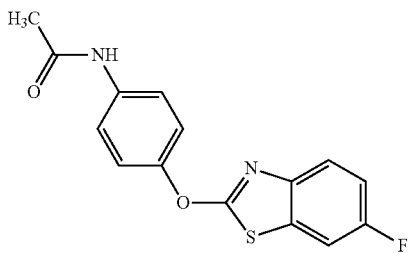 [SMILES: CC(=O)Nc1ccc(Oc2nc3ccc(F)cc3s2)cc1] | N-{4-[(6-fluoro-1,3-benzothiazol-2-yl)oxy]phenyl}acetamide |

TABLE 1-continued

Arylphenoxypropionate Derivatives

| | | |
|---|---|---|
| NZ-419 | | 2-{4-[(6-fluoro-1,3-benzothiazol-2-yl)oxy]-2-oxo-1,2-dihydropyridin-1-yl}-N-methylacetamide |
| NZ-418 | | 2-{4-[(6-fluoro-1,3-benzothiazol-2-yl)oxy]-2-oxo-1,2-dihydropyridin-1-yl}acetic acid |
| NZ-417 | | 2-amino-N-{4-[(6-fluoro-1,3-benzothiazol-2-yl)oxy]phenyl}acetamide |
| NZ-416 | | 3-amino-N-{4-[(6-fluoro-1,3-benzothiazol-2-yl)oxy]phenyl}propanamide |
| NZ-415 | | tert-butyl N-[({4-[(6-fluoro-1,3-benzothiazol-2-yl)oxy]phenyl}carbamoyl)methyl]carbamate |
| NZ-414 | | tert-butyl N-[2-({4-[(6-fluoro-1,3-benzothiazol-2-yl)oxy]phenyl}carbamoyl)ethyl]carbamate |
| NZ-413 | | 4-[(6-fluoro-1,3-benzothiazol-2-yl)oxy]aniline |

TABLE 1-continued

Arylphenoxypropionate Derivatives

| NZ-412 | | tert-butyl N-{4-[(6-fluoro-1,3-benzothiazol-2-yl)oxy]phenyl}carbamate |
| NZ-411 | | 2-{4-[(5,6-difluoro-1,3-benzothiazol-2-yl)oxy]-2-fluorophenyl}-N-methylacetamide |
| NZ-410 | | 2-{2-fluoro-4-[(6-fluoro-1,3-benzothiazol-2-yl)oxy]phenyl}-N-methylacetamide |
| NZ-409 | | 2-{4-[(5,6-difluoro-1,3-benzothiazol-2-yl)oxy]phenyl}-1-(4-methylpiperazin-1-yl)ethan-1-one |
| NZ-408 | | 2-{4-[(6-fluoro-1,3-benzothiazol-2-yl)oxy]-2-hydroxyphenyl}-N-methylpropanamide |

TABLE 1-continued

Arylphenoxypropionate Derivatives

| | | |
|---|---|---|
| NZ-407 | | 2-{4-[(5,6-difluoro-1,3-benzothiazol-2-yl)oxy]-2-hydroxyphenyl}-N-(propan-2-yl)acetamide |
| NZ-406 | | 2-{2-[(6-fluoro-1,3-benzothiazol-2-yl)oxy]-4-hydroxyphenyl}-N-(propan-2-yl)acetamide |
| NZ-405 | | 2-{4-[(6-fluoro-1,3-benzothiazol-2-yl)oxy]-2-hydroxyphenyl}-N-(propan-2-yl)acetamide |
| NZ-404 | | 2-{4-[(6-chloro-1,3-benzothiazol-2-yl)oxy]-2-oxo-1,2-dihydropyridin-1-yl}-N-(propan-2-yl)acetamide |
| NZ-403 | | 2-{4-[(5,6-difluoro-1,3-benzothiazol-2-yl)oxy]phenyl}-N-(propan-2-yl)acetamide |
| NZ-402 | | 2-{4-[(6-chloroquinoxalin-2-yl)oxy]-2-hydroxyphenyl}-N-methylacetamide |
| NZ-401 | | 2-{4-[(5,6-difluoro-1,3-benzothiazol-2-yl)oxy]-2-hydroxyphenyl}-N-methylacetamide |

TABLE 1-continued

Arylphenoxypropionate Derivatives

| | | |
|---|---|---|
| NZ-400 | 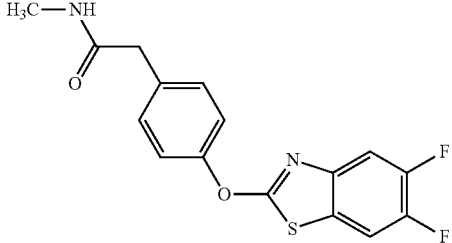 [SMILES: CNC(=O)Cc1ccc(Oc2nc3cc(F)c(F)cc3s2)cc1] | 2-{4-[(5,6-difluoro-1,3-benzothiazol-2-yl)oxy]phenyl}-N-methylacetamide |
| NZ-399 | 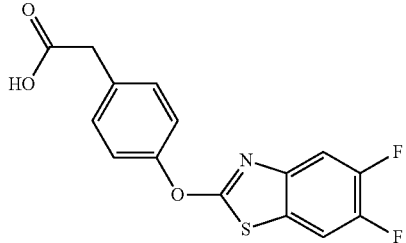 [SMILES: O=C(O)Cc1ccc(Oc2nc3cc(F)c(F)cc3s2)cc1] | 2-{4-[(5,6-difluoro-1,3-benzothiazol-2-yl)oxy]phenyl}acetic acid |
| NZ-398 | 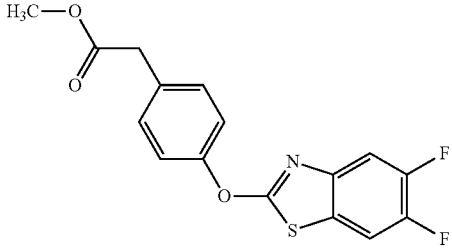 [SMILES: COC(=O)Cc1ccc(Oc2nc3cc(F)c(F)cc3s2)cc1] | methyl 2-{4-[(5,6-difluoro-1,3-benzothiazol-2-yl)oxy]phenyl}acetate |
| NZ-397 | 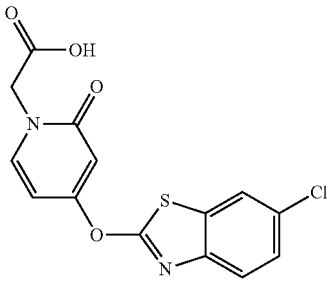 [SMILES: O=C(O)Cn1ccc(Oc2nc3ccc(Cl)cc3s2)cc1=O] | 2-{4-[(6-chloro-1,3-benzothiazol-2-yl)oxy]-2-oxo-1,2-dihydropyridin-1-yl}acetic acid |
| NZ-396 | 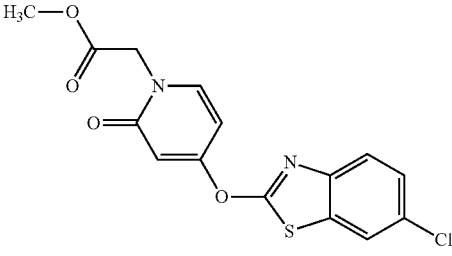 [SMILES: COC(=O)Cn1ccc(Oc2nc3ccc(Cl)cc3s2)cc1=O] | methyl 2-{4-[(6-chloro-1,3-benzothiazol-2-yl)oxy]-2-oxo-1,2-dihydropyridin-1-yl}acetate |
| NZ-395 | 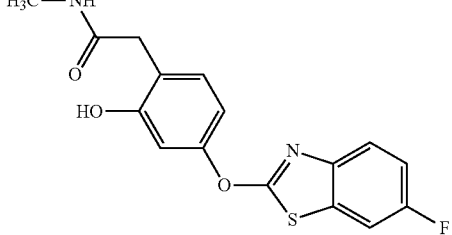 | 2-{4-[(6-fluoro-1,3-benzothiazol-2-yl)oxy]-2-hydroxyphenyl}-N-methylacetamide |

TABLE 1-continued

Arylphenoxypropionate Derivatives

| | | |
|---|---|---|
| NZ-394 | 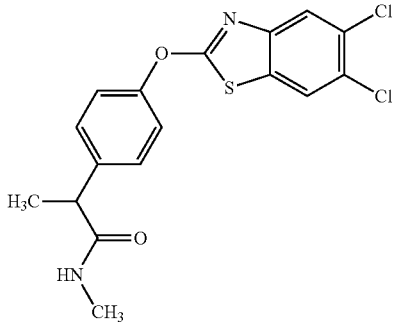 [SMILES: CNC(=O)C(C)c1ccc(Oc2nc3cc(Cl)c(Cl)cc3s2)cc1] | 2-{4-[(5,6-dichloro-1,3-benzothiazol-2-yl)oxy]phenyl}-N-methylpropanamide |
| NZ-393 | 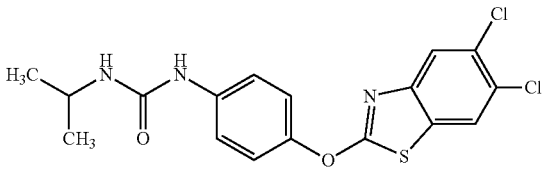 [SMILES: CC(C)NC(=O)Nc1ccc(Oc2nc3cc(Cl)c(Cl)cc3s2)cc1] | 1-{4-[(5,6-dichloro-1,3-benzothiazol-2-yl)oxy]phenyl}-3-(propan-2-yl)urea |
| NZ-392 | 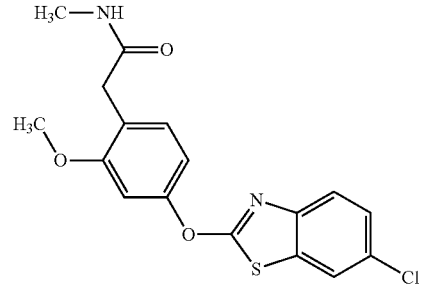 [SMILES: CNC(=O)Cc1ccc(Oc2nc3ccc(Cl)cc3s2)cc1OC] | 2-{4-[(6-chloro-1,3-benzothiazol-2-yl)oxy]-2-methoxyphenyl}-N-methylacetamide |
| NZ-391 | 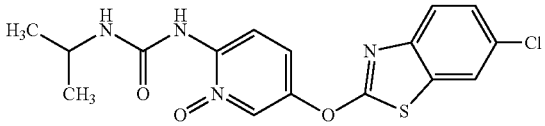 [SMILES: CC(C)NC(=O)Nc1ccc(Oc2nc3ccc(Cl)cc3s2)c[n+]1[O-]] | 1-{5-[(6-chloro-1,3-benzothiazol-2-yl)oxy]-1-oxo-1λ⁵-pyridin-2-yl}-3-(propan-2-yl)urea |
| NZ-390 | 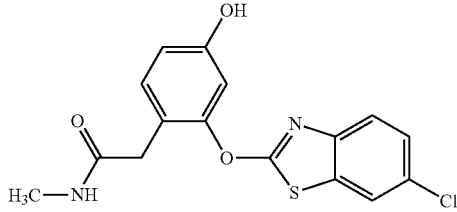 [SMILES: CNC(=O)Cc1ccc(O)cc1Oc1nc2ccc(Cl)cc2s1] | 2-{2-[(6-chloro-1,3-benzothiazol-2-yl)oxy]-4-hydroxyphenyl}-N-methylacetamide |
| NZ-389 | 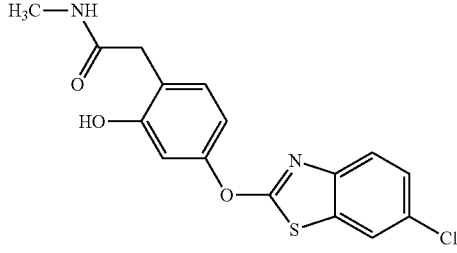 [SMILES: CNC(=O)Cc1ccc(Oc2nc3ccc(Cl)cc3s2)cc1O] | 2-{4-[(6-chloro-1,3-benzothiazol-2-yl)oxy]-2-hydroxyphenyl}-N-methylacetamide |
| NZ-388 | 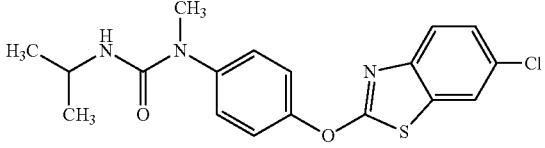 [SMILES: CC(C)NC(=O)N(C)c1ccc(Oc2nc3ccc(Cl)cc3s2)cc1] | 1-{4-[(6-chloro-1,3-benzothiazol-2-yl)oxy]phenyl}-1-methyl-3-(propan-2-yl)urea |

TABLE 1-continued

Arylphenoxypropionate Derivatives

| NZ-387 | 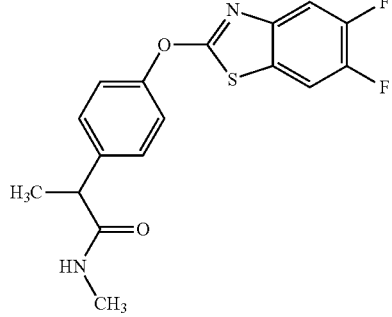 | 2-{4-[(5,6-difluoro-1,3-benzothiazol-2-yl)oxy]phenyl}-N-methylpropanamide |
| NZ-386 | 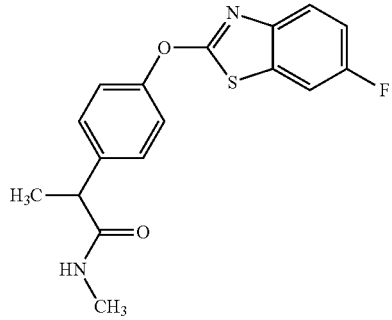 | 2-{4-[(6-fluoro-1,3-benzothiazol-2-yl)oxy]phenyl}-N-methylpropanamide |
| NZ-385 | 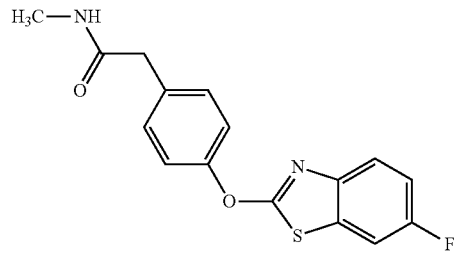 | 2-{4-[(6-fluoro-1,3-benzothiazol-2-yl)oxy]phenyl}-N-methylacetamide |
| NZ-383 | 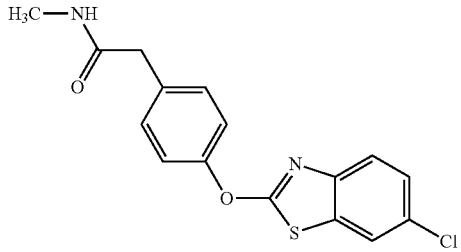 | 2-{4-[(6-chloro-1,3-benzothiazol-2-yl)oxy]phenyl}-N-methylacetamide |
| NZ-382 | 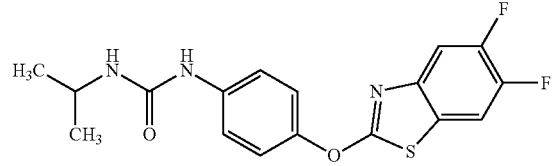 [SMILES: CC(C)NC(=O)Nc1ccc(Oc2nc3cc(F)c(F)cc3s2)cc1] | 1-{4-[(5,6-difluoro-1,3-benzothiazol-2-yl)oxy]phenyl}-3-(propan-2-yl)urea |
| NZ-381 | 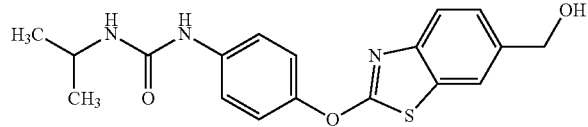 [SMILES: CC(C)NC(=O)Nc1ccc(Oc2nc3ccc(CO)cc3s2)cc1] | 1-(4-{[6-(hydroxymethyl)-1,3-benzothiazol-2-yl]oxy}phenyl)-3-(propan-2-yl)urea |

TABLE 1-continued

Arylphenoxypropionate Derivatives

| | | |
|---|---|---|
| NZ-380 | | 1-{4-[(6-methanesulfonyl-1,3-benzothiazol-2-yl)oxy]phenyl}-3-(propan-2-yl)urea |
| NZ-379 | | 3-(propan-2-yl)-1-(4-{[6-(trifluoromethyl)-1,3-benzothiazol-2-yl]oxy}phenyl)urea |
| NZ-378 | | ethyl 2-(4-{[(propan-2-yl)carbamoyl]amino}phenoxy)-1,3-benzothiazole-6-carboxylate |
| NZ-377 | | 1-{4-[(6-cyano-1,3-benzothiazol-2-yl)oxy]phenyl}-3-(propan-2-yl)urea |
| NZ-376 | | 1-{4-[(5-chloro-1,3-benzothiazol-2-yl)oxy]phenyl}-3-(propan-2-yl)urea |
| NZ-374 | | 1-{4-[(4-fluoro-1,3-benzothiazol-2-yl)oxy]phenyl}-3-(propan-2-yl)urea |

TABLE 1-continued
Arylphenoxypropionate Derivatives
NZ-373
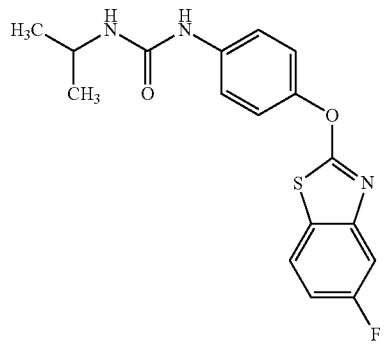 [SMILES: CC(C)NC(=O)Nc1ccc(Oc2nc3cc(F)ccc3s2)cc1]
1-{4-[(5-fluoro-1,3-benzothiazol-2-yl)oxy]phenyl}-3-(propan-2-yl)urea
NZ-372
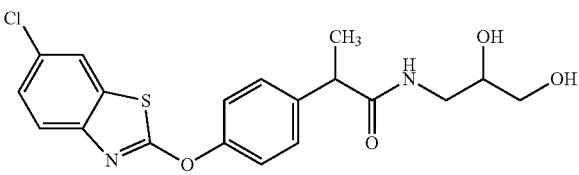 [SMILES: CC(C(=O)NCC(O)CO)c1ccc(Oc2nc3ccc(Cl)cc3s2)cc1]
2-{4-[(6-chloro-1,3-benzothiazol-2-yl)oxy]phenyl}-N-(2,3-dihydroxypropyl)propanamide
NZ-371
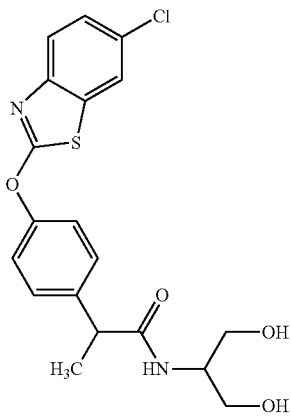 [SMILES: CC(C(=O)NC(CO)CO)c1ccc(Oc2nc3ccc(Cl)cc3s2)cc1]
2-{4-[(6-chloro-1,3-benzothiazol-2-yl)oxy]phenyl}-N-(1,3-dihydroxypropan-2-yl)propanamide
NZ-370
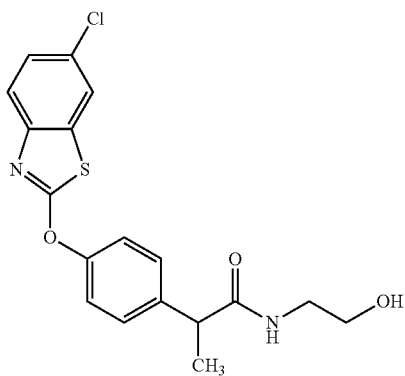 [SMILES: CC(C(=O)NCCO)c1ccc(Oc2nc3ccc(Cl)cc3s2)cc1]
2-{4-[(6-chloro-1,3-benzothiazol-2-yl)oxy]phenyl}-N-(2-hydroxyethyl)propanamide TABLE 1-continued
Arylphenoxypropionate Derivatives
| | | |
|---|---|---|
| NZ-369 | 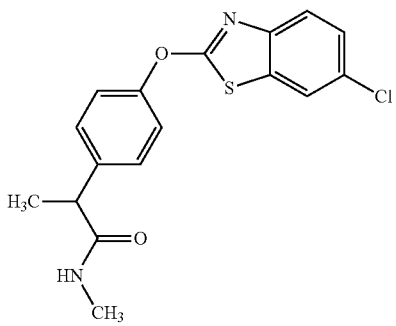 | 2-{4-[(6-chloro-1,3-benzothiazol-2-yl)oxy]phenyl}-N-methylpropanamide |
| NZ-368 | 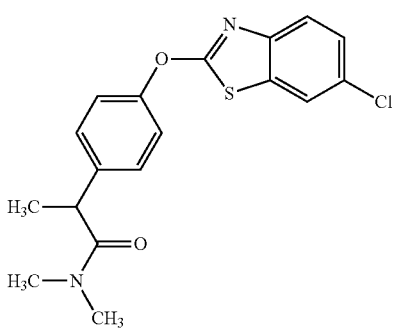 [SMILES: CC(C(=O)N(C)C)c1ccc(Oc2nc3ccc(Cl)cc3s2)cc1] | 2-{4-[(6-chloro-1,3-benzothiazol-2-yl)oxy]phenyl}-N,N-dimethylpropanamide |
| NZ-366 | 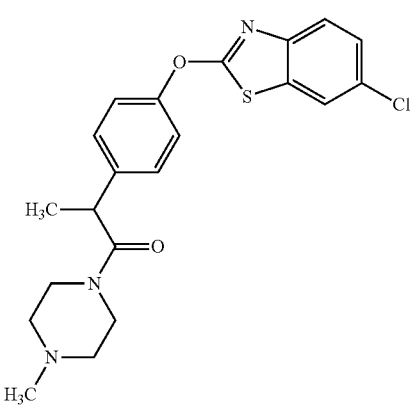 [SMILES: CC(C(=O)N1CCN(C)CC1)c1ccc(Oc2nc3ccc(Cl)cc3s2)cc1] | 2-{4-[(6-chloro-1,3-benzothiazol-2-yl)oxy]phenyl}-1-(4-methylpiperazin-1-yl)propan-1-one |
| NZ-365 | 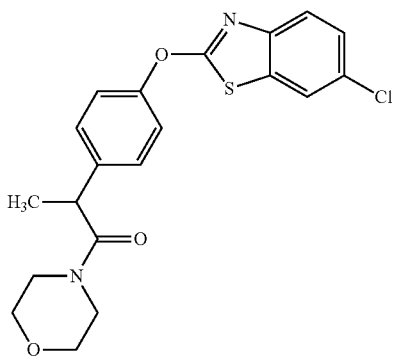 [SMILES: CC(C(=O)N1CCOCC1)c1ccc(Oc2nc3ccc(Cl)cc3s2)cc1] | 2-{4-[(6-chloro-1,3-benzothiazol-2-yl)oxy]phenyl}-1-(morpholin-4-yl)propan-1-one |

TABLE 1-continued

Arylphenoxypropionate Derivatives

| NZ-364 | 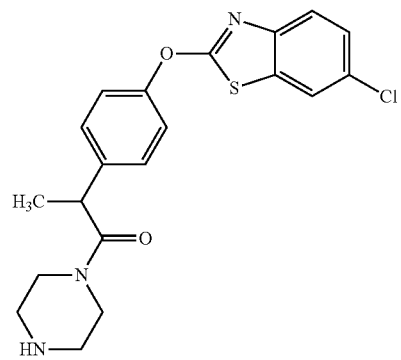 [SMILES: CC(C(=O)N1CCNCC1)c1ccc(Oc2nc3ccc(Cl)cc3s2)cc1] | 2-{4-[(6-chloro-1,3-benzothiazol-2-yl)oxy]phenyl}-1-(piperazin-1-yl)propan-1-one |
| --- | --- | --- |
| NZ-363 | 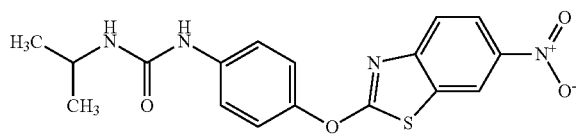 [SMILES: CC(C)NC(=O)Nc1ccc(Oc2nc3ccc([N+](=O)[O-])cc3s2)cc1] | 1-{4-[(6-nitro-1,3-benzothiazol-2-yl)oxy]phenyl}-3-(propan-2-yl)urea |
| NZ-362 | 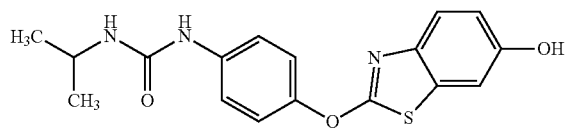 [SMILES: CC(C)NC(=O)Nc1ccc(Oc2nc3ccc(O)cc3s2)cc1] | 1-{4-[(6-hydroxy-1,3-benzothiazol-2-yl)oxy]phenyl}-3-(propan-2-yl)urea |
| NZ-361 | 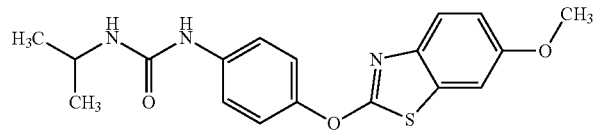 [SMILES: COc1ccc2nc(Oc3ccc(NC(=O)NC(C)C)cc3)sc2c1] | 1-{4-[(6-methoxy-1,3-benzothiazol-2-yl)oxy]phenyl}-3-(propan-2-yl)urea |
| NZ-360 | 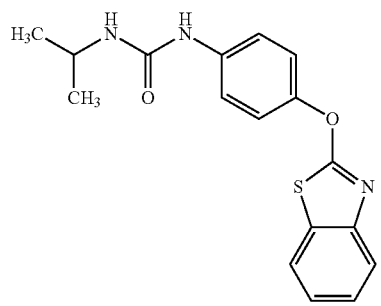 [SMILES: CC(C)NC(=O)Nc1ccc(Oc2nc3ccccc3s2)cc1] | 1-[4-(1,3-benzothiazol-2-yloxy)phenyl]-3-(propan-2-yl)urea |
| NZ-359 | 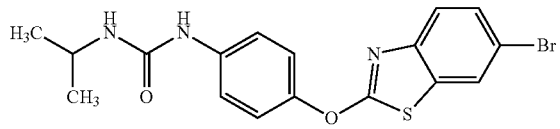 [SMILES: CC(C)NC(=O)Nc1ccc(Oc2nc3ccc(Br)cc3s2)cc1] | 1-{4-[(6-bromo-1,3-benzothiazol-2-yl)oxy]phenyl}-3-(propan-2-yl)urea |
| NZ-358 | 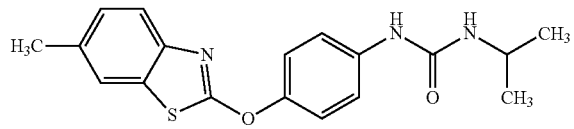 [SMILES: Cc1ccc2nc(Oc3ccc(NC(=O)NC(C)C)cc3)sc2c1] | 1-{4-[(6-methyl-1,3-benzothiazol-2-yl)oxy]phenyl}-3-(propan-2-yl)urea |

TABLE 1-continued
Arylphenoxypropionate Derivatives
| NZ-357 | 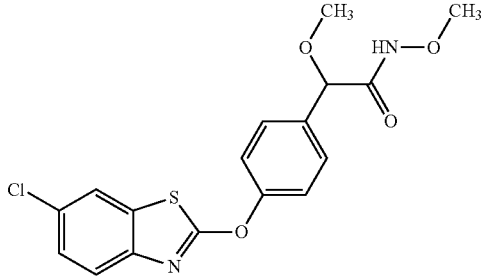 [SMILES: CONC(=O)C(OC)c1ccc(Oc2nc3ccc(Cl)cc3s2)cc1] | 2-{4-[(6-chloro-1,3-benzothiazol-2-yl)oxy]phenyl}-N,2-dimethoxyacetamide |
| NZ-356 | 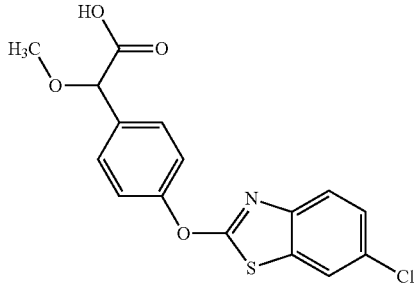 [SMILES: COC(C(=O)O)c1ccc(Oc2nc3ccc(Cl)cc3s2)cc1] | 2-{4-[(6-chloro-1,3-benzothiazol-2-yl)oxy]phenyl}-2-methoxyacetic acid |
| NZ-355 | 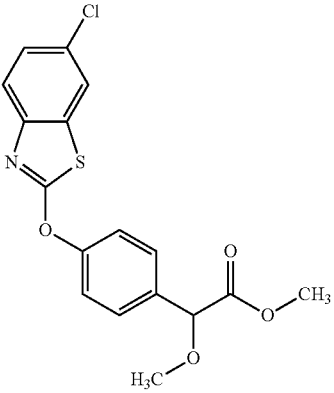 [SMILES: COC(=O)C(OC)c1ccc(Oc2nc3ccc(Cl)cc3s2)cc1] | methyl 2-{4-[(6-chloro-1,3-benzothiazol-2-yl)oxy]phenyl}-2-methoxyacetate |
| NZ-354 | 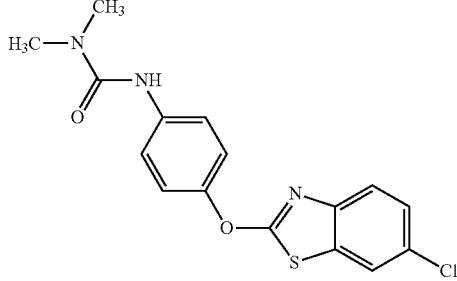 [SMILES: CN(C)C(=O)Nc1ccc(Oc2nc3ccc(Cl)cc3s2)cc1] | 1-{4-[(6-chloro-1,3-benzothiazol-2-yl)oxy]phenyl}-3,3-dimethylurea |
| NZ-353 | 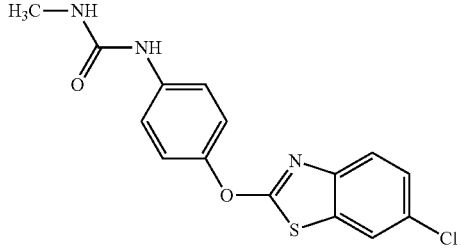 | 1-{4-[(6-chloro-1,3-benzothiazol-2-yl)oxy]phenyl}-3-methylurea |

TABLE 1-continued

Arylphenoxypropionate Derivatives

| | | |
|---|---|---|
| NZ-352 | 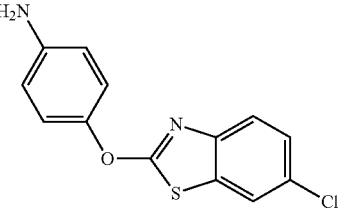 | 4-[(6-chloro-1,3-benzothiazol-2-yl)oxy]aniline |
| NZ-351 | 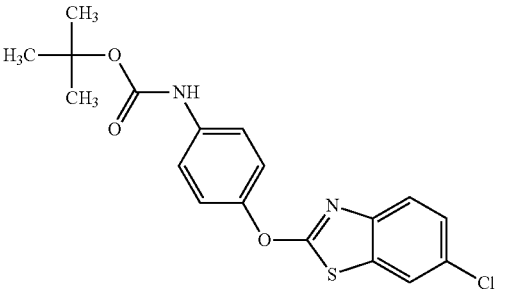 [SMILES: CC(C)(C)OC(=O)Nc1ccc(Oc2nc3ccc(Cl)cc3s2)cc1] | tert-butyl N-{4-[(6-chloro-1,3-benzothiazol-2-yl)oxy]phenyl}carbamate |
| NZ-350 | 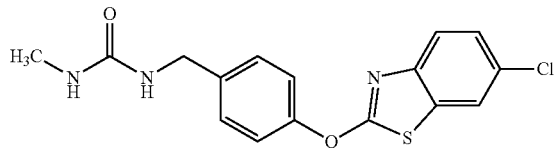 [SMILES: CNC(=O)NCc1ccc(Oc2nc3ccc(Cl)cc3s2)cc1] | 1-({4-[(6-chloro-1,3-benzothiazol-2-yl)oxy]phenyl}methyl)-3-methylurea |
| NZ-349 | 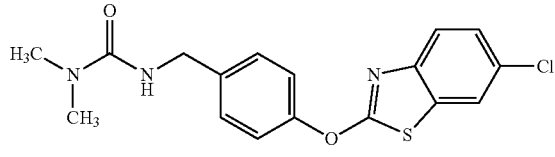 [SMILES: CN(C)C(=O)NCc1ccc(Oc2nc3ccc(Cl)cc3s2)cc1] | 1-({4-[(6-chloro-1,3-benzothiazol-2-yl)oxy]phenyl}methyl)-3,3-dimethylurea |
| NZ-348 | 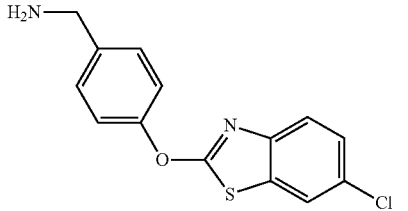 [SMILES: NCc1ccc(Oc2nc3ccc(Cl)cc3s2)cc1] | {4-[(6-chloro-1,3-benzothiazol-2-yl)oxy]phenyl}methanamine |
| NZ-347 | 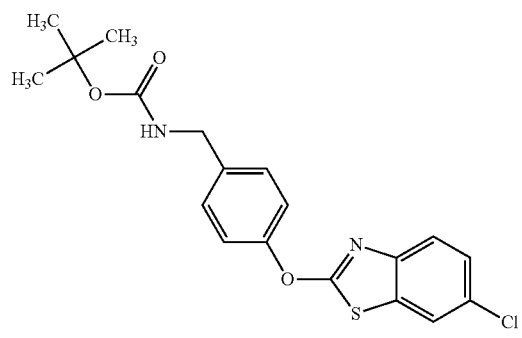 [SMILES: CC(C)(C)OC(=O)NCc1ccc(Oc2nc3ccc(Cl)cc3s2)cc1] | tert-butyl N-({4-[(6-chloro-1,3-benzothiazol-2-yl)oxy]phenyl}methyl)carbamate |
| NZ-346 | 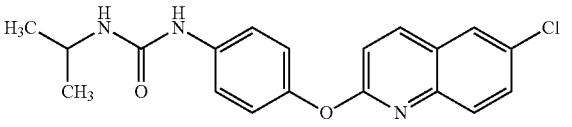 [SMILES: CC(C)NC(=O)Nc1ccc(Oc2ccc3cc(Cl)ccc3n2)cc1] | 1-{4-[(6-chloroquinolin-2-yl)oxy]phenyl}-3-(propan-2-yl)urea |

TABLE 1-continued

Arylphenoxypropionate Derivatives

| | | |
|---|---|---|
| NZ-345 | | 1-{4-[(6-fluoroquinoxalin-2-yl)oxy]phenyl}-3-(propan-2-yl)urea |
| NZ-344 | | 1-{4-[(6-chloroquinoxalin-2-yl)oxy]phenyl}-3-methoxyurea |
| NZ-343 | | 1-{4-[(6-chloroquinoxalin-2-yl)oxy]phenyl}-3,3-dimethylurea |
| NZ-342 | | 1-{4-[(6-chloroquinoxalin-2-yl)oxy]phenyl}-3-methylurea |
| NZ-341 | | 1-{4-[(6-chloro-1,3-benzothiazol-2-yl)oxy]phenyl}imidazolidin-2-one |
| NZ-338 | | 2-{4-[(6-chloro-1,3-benzothiazol-2-yl)oxy]phenyl}-2-hydroxy-N-methoxyacetamide |

TABLE 1-continued

Arylphenoxypropionate Derivatives

| NZ-337 | | 2-{4-[(6-chloro-1,3-benzothiazol-2-yl)oxy]phenyl}-2-hydroxyacetic acid |
| NZ-336 | | methyl 2-{4-[(6-chloro-1,3-benzothiazol-2-yl)oxy]phenyl}-2-hydroxyacetate |
| NZ-335 | | N-methoxy-2-{4-[(6-methoxy-1,3-benzothiazol-2-yl)oxy]phenyl}propanamide |
| NZ-334 | | 2-{4-[(6-methoxy-1,3-benzothiazol-2-yl)oxy]phenyl}propanoic acid |
| NZ-333 | | methyl 2-{4-[(6-methoxy-1,3-benzothiazol-2-yl)oxy]phenyl}propanoate |
| NZ-332 | | 1-{4-[(6-fluoro-1,3-benzothiazol-2-yl)oxy]phenyl}-3-(propan-2-yl)urea |
| NZ-331 | | 1-{4-[(6-chloro-1,3-benzothiazol-2-yl)oxy]phenyl}-3-(propan-2-yl)urea |

TABLE 1-continued

Arylphenoxypropionate Derivatives

| NZ-330 | | 2-{4-[(6-fluoro-1,3-benzothiazol-2-yl)oxy]phenyl}-N-methoxypropanamide |
| --- | --- | --- |
| NZ-329 | | 2-{4-[(6-fluoro-1,3-benzothiazol-2-yl)oxy]phenyl}propanoic acid |
| NZ-328 | | methyl 2-{4-[(6-fluoro-1,3-benzothiazol-2-yl)oxy]phenyl}propanoate |
| NZ-327 | | 2-{4-[(6-chloro-1,3-benzothiazol-2-yl)oxy]phenyl}-N-(propan-2-yl)propanamide |
| NZ-326 | | 2-{4-[(6-chloroquinoxalin-2-yl)oxy]phenoxy}-N-(propan-2-yloxy)acetamide |
| NZ-325 | | (Z)-2-{4-[(6-chloroquinoxalin-2-yl)oxy]phenoxy}-N-methoxyethenecarbonimidoyl chloride |

TABLE 1-continued

Arylphenoxypropionate Derivatives

| NZ-323 | | 2-{4-[(6-chloroquinoxalin-2-yl)oxy]phenoxy}-N-(cyclopropylmethoxy)acetamide |
| --- | --- | --- |
| NZ-322 | | 1-{4-[(6-chloroquinoxalin-2-yl)oxy]phenyl}-3-(propan-2-yl)urea |
| NZ-321 | | tert-butyl N-{4-[(6-chloroquinoxalin-2-yl)oxy]phenyl}carbamate |
| NZ-320 | | N-methoxy-2-oxo-7-phenoxy-2H-chromene-3-carboxamide |
| NZ-319 | | 2-{4-[(6-chloro-1,3-benzothiazol-2-yl)oxy]phenoxy}-N-methoxy-2-methylpropanamide |
| NZ-318 | | 2-{4-[(6-chloro-1,3-benzothiazol-2-yl)oxy]phenoxy}-2-methylpropanoic acid |

TABLE 1-continued

Arylphenoxypropionate Derivatives

| | | |
|---|---|---|
| NZ-317 | | methyl 2-{4-[(6-chloro-1,3-benzothiazol-2-yl)oxy]phenoxy}-2-methylpropanoate |
| NZ-316 | | 2-{4-[(6-chloroquinoxalin-2-yl)oxy]phenoxy}-N-methoxy-2-methylpropanamide |
| NZ-315 | | 2-{4-[(6-chloroquinoxalin-2-yl)oxy]phenoxy}-2-methylpropanoic acid |
| NZ-314 | | methyl 2-{4-[(6-chloroquinoxalin-2-yl)oxy]phenoxy}-2-methylpropanoate |
| NZ-313 | | 2-{4-[(6-chloro-1,3-benzothiazol-2-yl)oxy]phenyl}-N-methoxypropanamide |
| NZ-312 | | 2-{4-[(6-chloro-1,3-benzothiazol-2-yl)oxy]phenyl}propanoic acid |

TABLE 1-continued

Arylphenoxypropionate Derivatives

| NZ-311 | 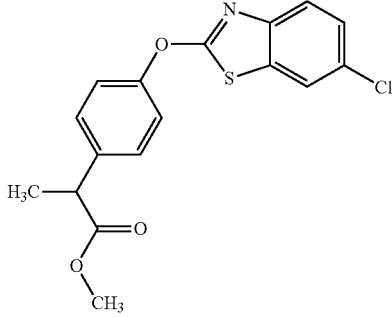 [SMILES: COC(=O)C(C)c1ccc(Oc2nc3ccc(Cl)cc3s2)cc1] | methyl 2-{4-[(6-chloro-1,3-benzothiazol-2-yl)oxy]phenyl}propanoate |
| --- | --- | --- |
| NZ-310 | 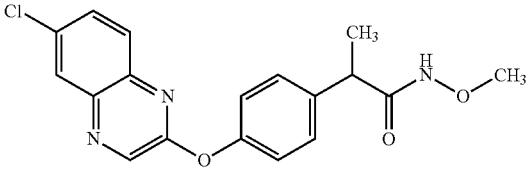 [SMILES: CONC(=O)C(C)c1ccc(Oc2cnc3cc(Cl)ccc3n2)cc1] | 2-{4-[(6-chloroquinoxalin-2-yl)oxy]phenyl}-N-methoxypropanamide |
| NZ-309 | 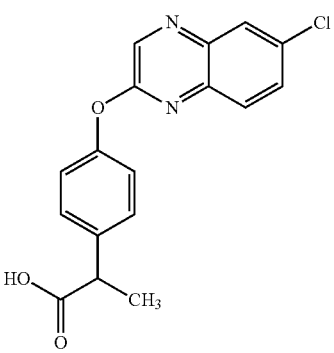 [SMILES: CC(C(=O)O)c1ccc(Oc2cnc3cc(Cl)ccc3n2)cc1] | 2-{4-[(6-chloroquinoxalin-2-yl)oxy]phenyl}propanoic acid |
| NZ-308 | 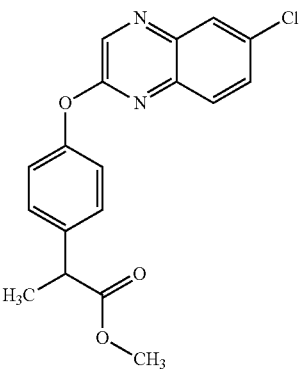 [SMILES: COC(=O)C(C)c1ccc(Oc2cnc3cc(Cl)ccc3n2)cc1] | methyl 2-{4-[(6-chloroquinoxalin-2-yl)oxy]phenyl}propanoate |
| NZ-307 | 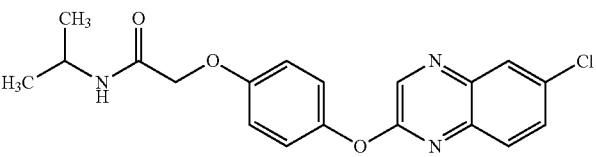 [SMILES: CC(C)NC(=O)COc1ccc(Oc2cnc3cc(Cl)ccc3n2)cc1] | 2-{4-[(6-chloroquinoxalin-2-yl)oxy]phenoxy}-N-(propan-2-yl)acetamide |
| NZ-306 | 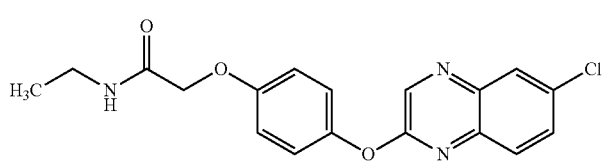 [SMILES: CCNC(=O)COc1ccc(Oc2cnc3cc(Cl)ccc3n2)cc1] | 2-{4-[(6-chloroquinoxalin-2-yl)oxy]phenoxy}-N-ethylacetamide |

TABLE 1-continued

| | Arylphenoxypropionate Derivatives | |
|---|---|---|
| NZ-305 | | 2-{4-[(6-fluoro-1,3-benzothiazol-2-yl)oxy]phenoxy}-N-methoxyacetamide |
| NZ-304 | | 2-{4-[(6-fluoro-1,3-benzothiazol-2-yl)oxy]phenoxy}acetic acid |
| NZ-303 | | methyl 2-{4-[(6-fluoro-1,3-benzothiazol-2-yl)oxy]phenoxy}acetate |
| NZ-302 | | methyl 2-{4-[(6-chloro-1,3-benzoxazol-2-yl)oxy]phenyl}acetate |
| NZ-301 | | 2-{4-[(6-chloroquinoxalin-2-yl)oxy]phenyl}-N-methoxyacetamide |
| NZ-300 | | 2-{4-[(6-fluoro-1,3-benzothiazol-2-yl)oxy]phenyl}-N-methoxyacetamide |
| NZ-299 | | 2-{4-[(6-fluoro-1,3-benzothiazol-2-yl)oxy]phenyl}acetic acid |

TABLE 1-continued

Arylphenoxypropionate Derivatives

| NZ-298 | 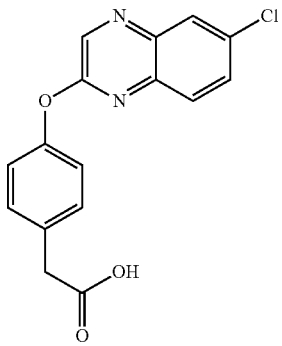 [SMILES: O=C(O)Cc1ccc(Oc2cnc3cc(Cl)ccc3n2)cc1] | 2-{4-[(6-chloroquinoxalin-2-yl)oxy]phenyl}acetic acid |
| NZ-297 | 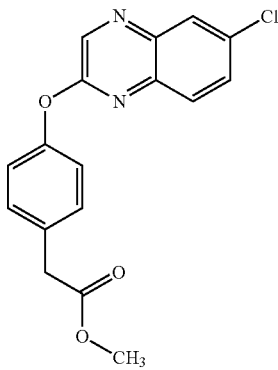 [SMILES: COC(=O)Cc1ccc(Oc2cnc3cc(Cl)ccc3n2)cc1] | methyl 2-{4-[(6-chloroquinoxalin-2-yl)oxy]phenyl}acetate |
| NZ-296 | 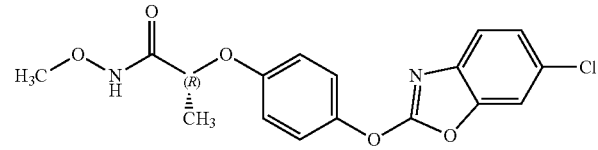 | (2R)-2-{4-[(6-chloro-1,3-benzoxazol-2-yl)oxy]phenoxy}-N-methoxypropanamide |
| NZ-295 | 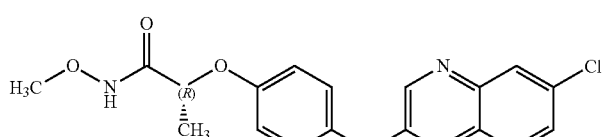 | (2R)-2-{4-[(6-chloroquinoxalin-2-yl)oxy]phenoxy}-N-methoxypropanamide |
| NZ-294 | 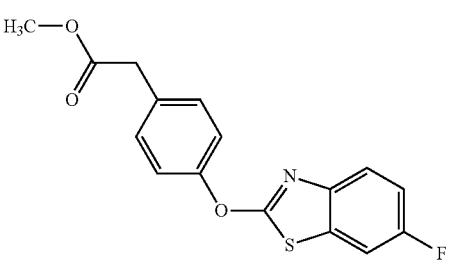 | methyl 2-{4-[(6-fluoro-1,3-benzothiazol-2-yl)oxy]phenyl}acetate |
| NZ-293 | 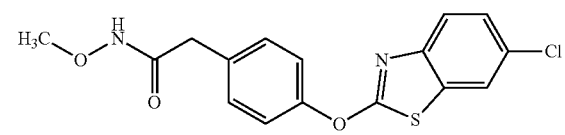 [SMILES: CONC(=O)Cc1ccc(Oc2nc3ccc(Cl)cc3s2)cc1] | 2-{4-[(6-chloro-1,3-benzothiazol-2-yl)oxy]phenyl}-N-methoxyacetamide |

TABLE 1-continued

| Arylphenoxypropionate Derivatives | | |
|---|---|---|
| NZ-292 | | 6-chloro-2-phenoxy-1,3-benzothiazole |
| NZ-291 | | 6-chloro-2-(3-methylphenoxy)-1,3-benzothiazole |
| NZ-290 | | 2-{4-[(6-chloroquinoxalin-2-yl)oxy]phenoxy}-N-methoxy-N-methylacetamide |
| NZ-289 | | (2R)-2-{4-[(6-fluoro-1,3-benzothiazol-2-yl)oxy]phenoxy}-N-methoxypropanamide |
| NZ-288 | | 4-[(6-chloro-1,3-benzothiazol-2-yl)oxy]benzoic acid |
| NZ-287 | | 2-{4-[(6-chloro-1,3-benzothiazol-2-yl)oxy]phenyl}acetic acid |
| NZ-286 | | 2-{4-[(6-chloroquinoxalin-2-yl)oxy]phenoxy}-N-hydroxyacetamide |

TABLE 1-continued

| Arylphenoxypropionate Derivatives | | |
|---|---|---|
| NZ-285 | | methyl 4-[(6-chloro-1,3-benzothiazol-2-yl)oxy]benzoate |
| NZ-284 | | methyl 2-{4-[(6-chloro-1,3-benzothiazol-2-yl)oxy]phenyl}acetate |
| NZ-283 | | (2E)-3-{4-[(6-chloro-1,3-benzothiazol-2-yl)oxy]phenyl}prop-2-enoic acid |
| NZ-282 | | 3-{4-[(6-chloro-1,3-benzothiazol-2-yl)oxy]phenyl}propanoic acid |
| NZ-281 | | methyl (2E)-3-{4-[(6-chloro-1,3-benzothiazol-2-yl)oxy]phenyl}prop-2-enoate |
| NZ-280 | | methyl 3-{4-[(6-chloro-1,3-benzothiazol-2-yl)oxy]phenyl}propanoate |

TABLE 1-continued

Arylphenoxypropionate Derivatives

| NZ-279 | 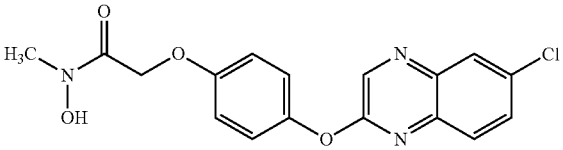 [SMILES: CN(O)C(=O)COc1ccc(Oc2cnc3cc(Cl)ccc3n2)cc1] | 2-{4-[(6-chloroquinoxalin-2-yl)oxy]phenoxy}-N-hydroxy-N-methylacetamide |
| NZ-278 | 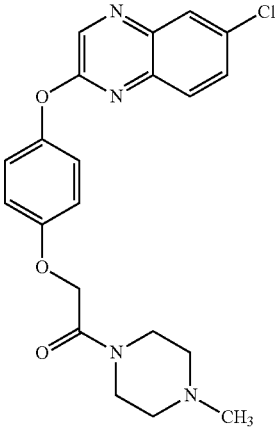 [SMILES: CN1CCN(C(=O)COc2ccc(Oc3cnc4cc(Cl)ccc4n3)cc2)CC1] | 2-{4-[(6-chloroquinoxalin-2-yl)oxy]phenoxy}-1-(4-methylpiperazin-1-yl)ethan-1-one |
| NZ-277 | 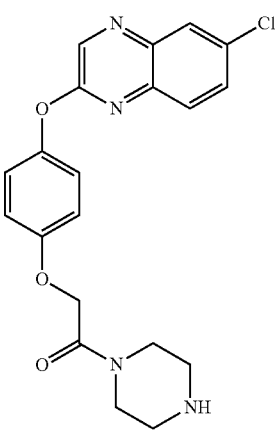 [SMILES: O=C(COc1ccc(Oc2cnc3cc(Cl)ccc3n2)cc1)N1CCNCC1] | 2-{4-[(6-chloroquinoxalin-2-yl)oxy]phenoxy}-1-(piperazin-1-yl)ethan-1-one |
| NZ-276 | 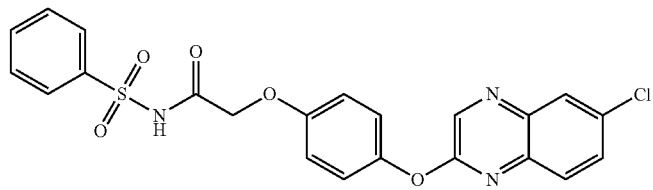 [SMILES: O=C(COc1ccc(Oc2cnc3cc(Cl)ccc3n2)cc1)NS(=O)(=O)c1ccccc1] | N-(benzenesulfonyl)-2-{4-[(6-chloroquinoxalin-2-yl)oxy]phenoxy}acetamide |
| NZ-275 | 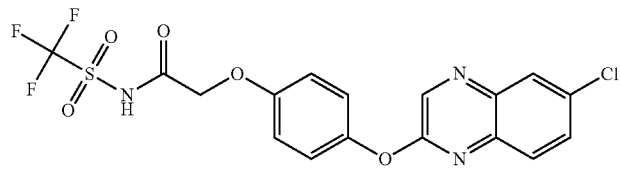 [SMILES: O=C(COc1ccc(Oc2cnc3cc(Cl)ccc3n2)cc1)NS(=O)(=O)C(F)(F)F] | 2-{4-[(6-chloroquinoxalin-2-yl)oxy]phenoxy}-N-trifluoromethanesulfonylacetamide |
| NZ-274 | 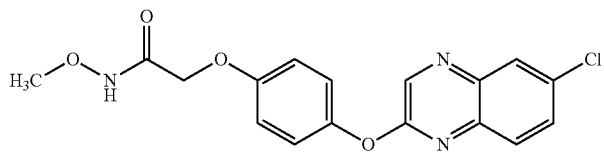 [SMILES: CONC(=O)COc1ccc(Oc2cnc3cc(Cl)ccc3n2)cc1] | 2-{4-[(6-chloroquinoxalin-2-yl)oxy]phenoxy}-N-methoxyacetamide |

TABLE 1-continued
Arylphenoxypropionate Derivatives
NZ-273 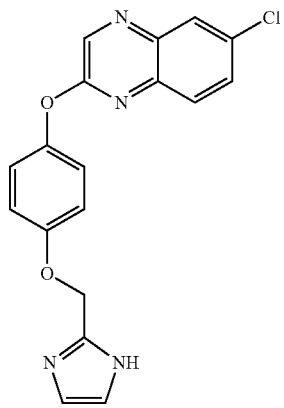 [SMILES: Clc1ccc2nc(Oc3ccc(OCc4ncc[nH]4)cc3)cnc2c1] 6-chloro-2-[4-(1H-imidazol-2-ylmethoxy)phenoxy]quinoxaline
NZ-272 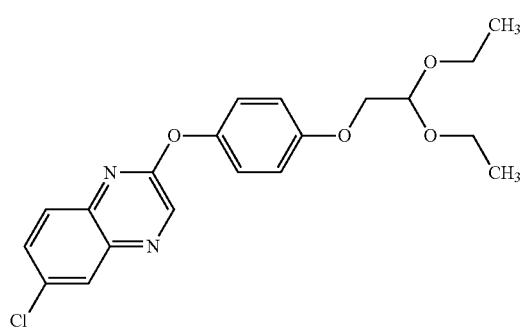 [SMILES: CCOC(COc1ccc(Oc2cnc3cc(Cl)ccc3n2)cc1)OCC] 6-chloro-2-[4-(2,2-diethoxyethoxy)phenoxy]quinoxaline
NZ-271 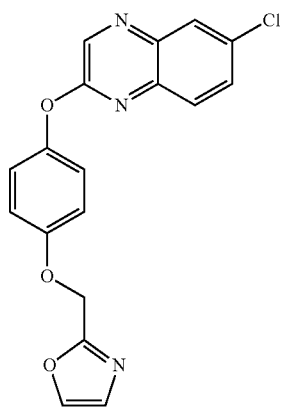 [SMILES: Clc1ccc2nc(Oc3ccc(OCc4ncco4)cc3)cnc2c1] 6-chloro-2-[4-(1,3-oxazol-2-ylmethoxy)phenoxy]quinoxaline
NZ-270 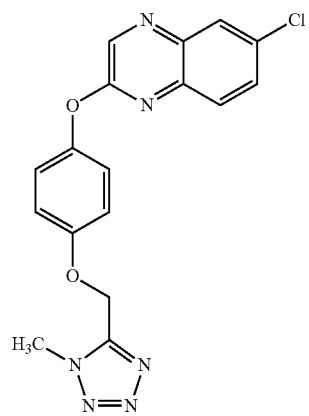 [SMILES: Cn1nnnc1COc1ccc(Oc2cnc3cc(Cl)ccc3n2)cc1] 6-chloro-2-{4-[(1-methyl-1H-1,2,3,4-tetrazol-5-yl)methoxy]phenoxy}quinoxaline TABLE 1-continued
Arylphenoxypropionate Derivatives
| | | |
|---|---|---|
| NZ-269 | 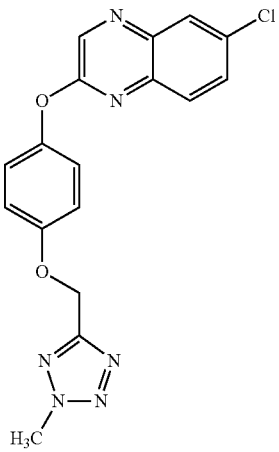 [SMILES: Cn1nnc(COc2ccc(Oc3cnc4cc(Cl)ccc4n3)cc2)n1] | 6-chloro-2-{4-[(2-methyl-2H-1,2,3,4-tetrazol-5-yl)methoxy]phenoxy}quinoxaline |
| NZ-268 | 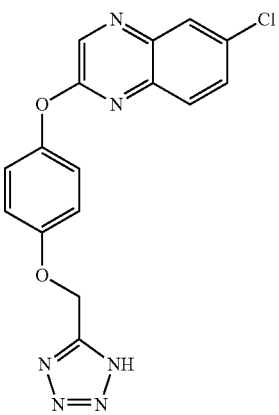 [SMILES: Clc1ccc2nc(Oc3ccc(OCc4nnn[nH]4)cc3)cnc2c1] | 6-chloro-2-[4-(1H-1,2,3,4-tetrazol-5-ylmethoxy)phenoxy]quinoxaline |
| NZ-267 | 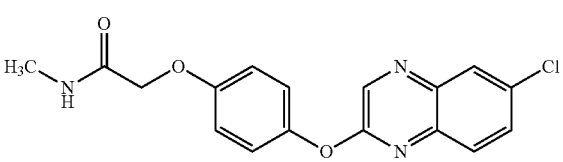 [SMILES: CNC(=O)COc1ccc(Oc2cnc3cc(Cl)ccc3n2)cc1] | 2-{4-[(6-chloroquinoxalin-2-yl)oxy]phenoxy}-N-methylacetamide |
| NZ-266 | 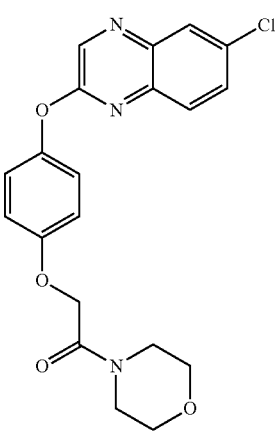 [SMILES: O=C(COc1ccc(Oc2cnc3cc(Cl)ccc3n2)cc1)N1CCOCC1] | 2-{4-[(6-chloroquinoxalin-2-yl)oxy]phenoxy}-1-(morpholin-4-yl)ethan-1-one |

TABLE 1-continued

Arylphenoxypropionate Derivatives

| NZ-265 | | 2-{4-[(6-chloroquinoxalin-2-yl)oxy]phenoxy}-1-(piperidin-1-yl)ethan-1-one |
| NZ-264 | | 1-{4-[(6-chloroquinoxalin-2-yl)oxy]phenoxy}propan-2-ol |
| NZ-263 | | 2-{4-[(6-chloroquinoxalin-2-yl)oxy]phenoxy}acetonitrile |
| NZ-262 | | 2-{4-[(6-chloroquinoxalin-2-yl)oxy]phenoxy}-N,N-dimethylacetamide |

TABLE 1-continued

Arylphenoxypropionate Derivatives

| | | |
|---|---|---|
| NZ-261 | 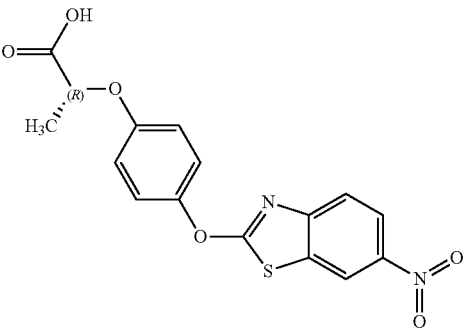 | (2R)-2-{4-[(6-nitro-1,3-benzothiazol-2-yl)oxy]phenoxy}propanoic acid |
| NZ-260 | 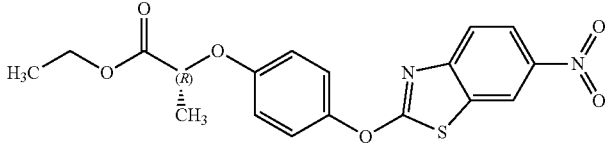 | ethyl (2R)-2-{4-[(6-nitro-1,3-benzothiazol-2-yl)oxy]phenoxy}propanoate |
| NZ-259 | 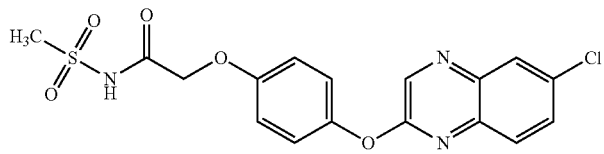 [SMILES: CS(=O)(=O)NC(=O)COc1ccc(Oc2cnc3cc(Cl)ccc3n2)cc1] | 2-{4-[(6-chloroquinoxalin-2-yl)oxy]phenoxy}-N-methanesulfonylacetamide |
| NZ-258 | 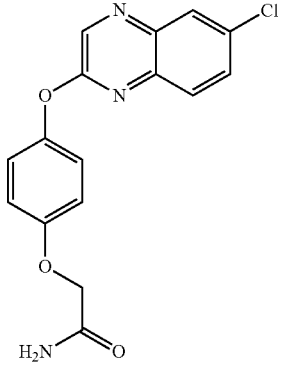 [SMILES: NC(=O)COc1ccc(Oc2cnc3cc(Cl)ccc3n2)cc1] | 2-{4-[(6-chloroquinoxalin-2-yl)oxy]phenoxy}acetamide |
| NZ-257 | 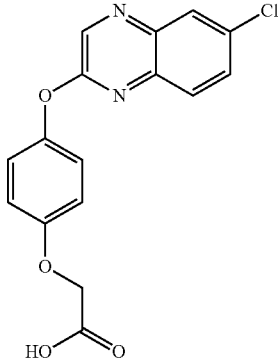 [SMILES: O=C(O)COc1ccc(Oc2cnc3cc(Cl)ccc3n2)cc1] | 2-{4-[(6-chloroquinoxalin-2-yl)oxy]phenoxy}acetic acid |
| NZ-256 | 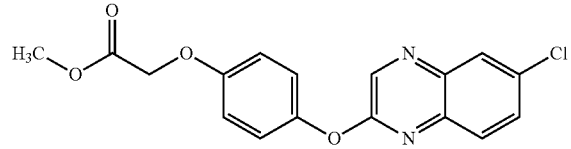 [SMILES: COC(=O)COc1ccc(Oc2cnc3cc(Cl)ccc3n2)cc1] | methyl 2-{4-[(6-chloroquinoxalin-2-yl)oxy]phenoxy}acetate |

TABLE 1-continued

Arylphenoxypropionate Derivatives

| | | |
|---|---|---|
| NZ-255 | 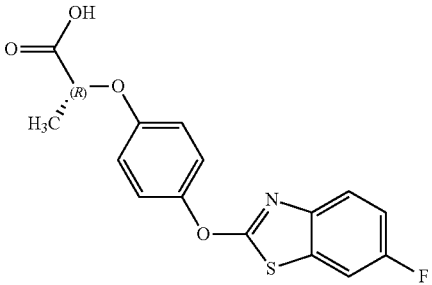 | (2R)-2-{4-[(6-fluoro-1,3-benzothiazol-2-yl)oxy]phenoxy}propanoic acid |
| NZ-254 | 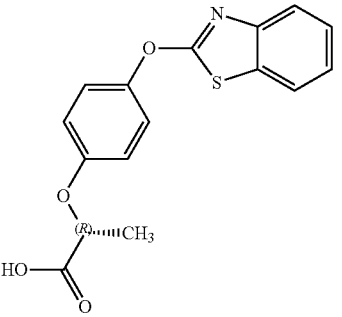 | (2R)-2-[4-(1,3-benzothiazol-2-yloxy)phenoxy]propanoic acid |
| NZ-253 | 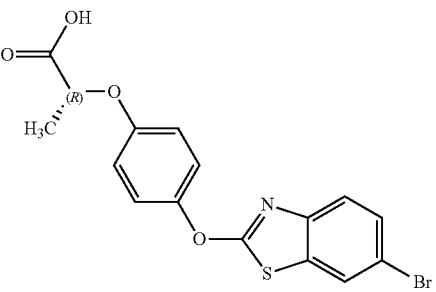 | (2R)-2-{4-[(6-bromo-1,3-benzothiazol-2-yl)oxy]phenoxy}propanoic acid |
| NZ-252 | 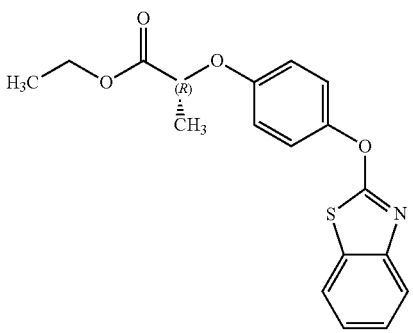 | ethyl (2R)-2-[4-(1,3-benzothiazol-2-yloxy)phenoxy]propanoate |
| NZ-251 | 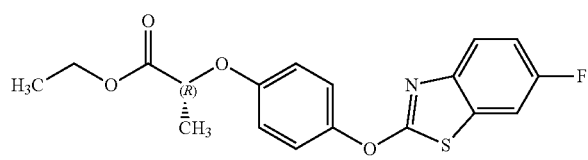 | ethyl (2R)-2-{4-[(6-fluoro-1,3-benzothiazol-2-yl)oxy]phenoxy}propanoate |
| NZ-250 | 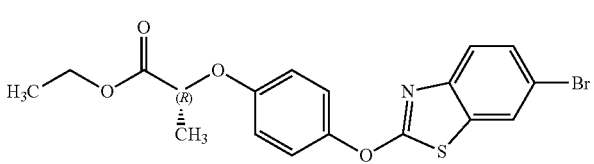 | ethyl (2R)-2-{4-[(6-bromo-1,3-benzothiazol-2-yl)oxy]phenoxy}propanoate |

TABLE 1-continued

Arylphenoxypropionate Derivatives

| | | |
|---|---|---|
| NZ-247 | 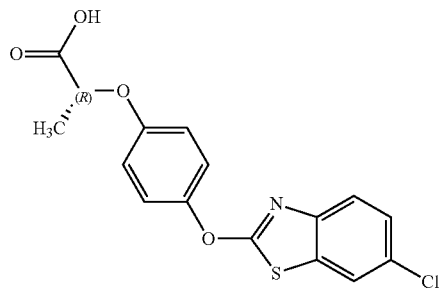 | (2R)-2-{4-[(6-chloro-1,3-benzothiazol-2-yl)oxy]phenoxy}propanoic acid |
| NZ-246 | 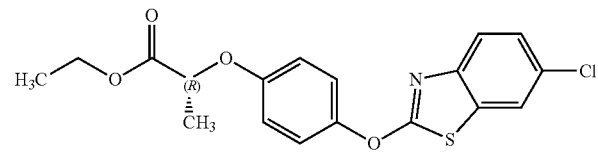 | ethyl (2R)-2-{4-[(6-chloro-1,3-benzothiazol-2-yl)oxy]phenoxy}propanoate |
| fenoxaprop-p-ethyl | 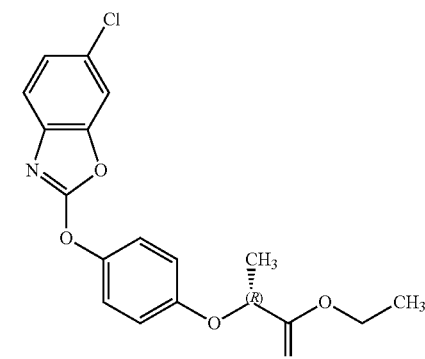 | ethyl (2R)-2-{4-[(6-chloro-1,3-benzoxazol-2-yl)oxy]phenoxy}propanoate |
| fenoxaprop-p | 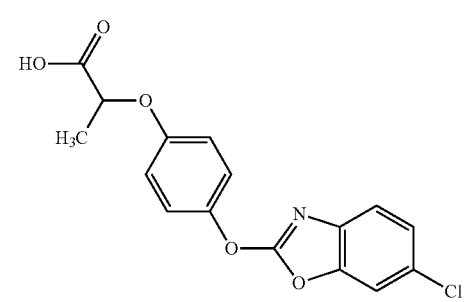 [SMILES: CC(Oc1ccc(Oc2nc3ccc(Cl)cc3o2)cc1)C(=O)O] | 2-{4-[(6-chloro-1,3-benzoxazol-2-yl)oxy]phenoxy}propanoic acid |

The present disclosure also includes pharmaceutically acceptable salts, hydrates, prodrugs, and mixtures of any of the above compositions. The term "pharmaceutically acceptable salt" refers to salts whose counter ion derives from pharmaceutically acceptable non-toxic acids and bases.

The arylphenoxypropionate derivatives, aryloxyphenoxyacetate derivatives, aryloxyphenylacetate derivatives, and substituted quinols which contain a basic moiety, such as, but not limited to an amine or a pyridine or imidazole ring, may form salts with a variety of organic and inorganic acids. Suitable pharmaceutically acceptable (i.e., non-toxic, physiologically acceptable) base addition salts for the compounds of the present invention include inorganic acids and organic acids. Examples include acetate, adipate, alginates, ascorbates, aspartates, benzenesulfonate (besylate), benzoate, bicarbonate, bisulfate, borates, butyrates, carbonate, camphorsulfonate, citrate, digluconates, dodecylsulfates, ethanesulfonate, fumarate, gluconate, glutamate, glycerophosphates, hemisulfates, heptanoates, hexanoates, hydrobromides, hydrochloride, hydroiodides, 2-hydroxyethanesulfonates, isethionate, lactate, maleate, malate, mandelate, methanesulfonate, 2-naphthalenesulfonates, nicotinates, mucate, nitrate, oxalates, pectinates, persulfates, 3-phenylpropionates, picrates, pivalates, propionates, pamoate, pantothenate, phosphate, salicylates, succinate, sulfate, sulfonates, tartrate, p-toluenesulfonate, and the like.

The arylphenoxypropionate derivatives, aryloxyphenoxyacetate derivatives, aryloxyphenylacetate derivatives, and substituted quinols which contain an acidic moiety, such as, but not limited to a carboxylic acid, may form salts with variety of organic and inorganic bases. Suitable pharmaceutically acceptable base addition salts for the compounds of the present invention include, but are not limited to, ammonium salts, metallic salts made from calcium, lithium, magnesium, potassium, sodium and zinc or organic salts made from lysine, N,N-dialkyl amino acid derivatives (e.g. N,N- dimethylglycine, piperidine-1-acetic acid and morpholine-4-acetic acid), N,N'-dibenzylethylenediamine, chloroprocaine, choline, diethanolamine, ethylenediamine, meglumine (N-methylglucamine), t-butylamine, dicyclohexylamine, hydrabamine, and procaine.

The arylphenoxypropionate derivatives, aryloxyphenoxyacetate derivatives, aryloxyphenylacetate derivatives, and substituted quinols, and salts thereof, may exist in their tautomeric form (for example, as an amide or imino ether). All such tautomeric forms are contemplated herein as part of the present invention.

The compounds described herein may contain asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as, their racemic and optically pure forms. Optically active (R)- and (S)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

Compositions of the present disclosure may also include a pharmaceutically acceptable carrier, in particular a carrier suitable for the intended mode of administration, or salts, buffers, or preservatives. Certain of the compounds disclosed herein are poorly soluble in water. Accordingly, aqueous compositions of the present disclosure may include solubility enhancers. Compositions for oral use may include components to enhance intestinal absorption. The overall formulation of the compositions may be based on the intended mode of administration. For instance, the composition may be formulated as a pill or capsule for oral ingestion. In other examples, the composition may be encapsulated, such as in a liposome or nanoparticle.

Compositions of the present disclosure may contain a sufficient amount of one or more one or more arylphenoxypropionate derivatives, one or more aryloxyphenoxyacetate derivatives, one or more aryloxyphenylacetate derivatives, one or more substituted quinols, or pharmaceutically acceptable salts, hydrates, or prodrugs thereof, or combinations thereof, to cause inhibition of a *mycobacterium* to occur when the composition is administered to the *mycobacterium*. The amount can vary depending on other components of the composition and their effects on drug availability in a patient, the amount of otherwise required to inhibit the *mycobacterium*, the intended mode of administration, the intended schedule for administration, any drug toxicity concerns, drug-drug interactions, such as interactions with other medications used by the patient, or the individual response of a patient. Many compositions may contain an amount well below levels at which toxicity to the patient becomes a concern.

The amount of arylphenoxypropionate derivative, aryloxyphenoxyacetate derivative, aryloxyphenylacetate derivative, substituted quinol, or pharmaceutically acceptable salt, hydrate, or prodrug thereof, or combination thereof, present in a composition may be measured in any of a number of ways. The amount may, for example, express concentration or total amount. Concentration may be for example, weight/weight, weight/volume, moles/weight, or moles/volume. Total amount may be total weight, total volume, or total moles. Typically, the amount may be expressed in a manner standard for the type of formulation or dosing regimen used.

*Mycobacterium* Inhibition Methods

The present disclosure also provides methods of inhibiting a *mycobacterium* using an arylphenoxypropionate derivative, aryloxyphenoxyacetate derivative, aryloxyphenylacetate derivative, substituted quinol, or pharmaceutically acceptable salt, hydrate, or prodrug thereof, or combination thereof. In certain embodiments in which a *mycobacterium* is inhibited by administration of an arylphenoxypropionate derivative, aryloxyphenoxyacetate derivative, aryloxyphenylacetate derivative, substituted quinol, or pharmaceutically acceptable salt, hydrate, or prodrug thereof, or combination thereof, the dosage and administration may be adequate to allow this inhibition. In certain embodiments, it may consist of regular administration of an amount of the arylphenoxypropionate derivative, aryloxyphenoxyacetate derivative, aryloxyphenylacetate derivative, substituted quinol, or pharmaceutically acceptable salt, hydrate, or prodrug thereof, or combination thereof, to maintain a certain level in the patient, the patient's blood, and/or a tissue in the patient. However, dosage amounts and the administration schedule may be adjusted based on other components of the composition and their effects on drug availability in a patient, the intended mode of administration, the intended schedule for administration, any drug toxicity concerns, and the patient's response to the drug.

Without limiting the compositions and methods of administration described herein, in certain embodiments, the arylphenoxypropionate derivative, aryloxyphenoxyacetate derivative, aryloxyphenylacetate derivative, substituted quinol, or pharmaceutically acceptable salt, hydrate, or prodrug thereof, or combination thereof, can exhibit its inhibitory effect on a *mycobacterium* by directly or indirectly inhibiting fatty acid biosynthesis. In certain embodiments, this inhibition is mediated by binding of the arylphenoxypropionate derivative, aryloxyphenoxyacetate derivative, aryloxyphenylacetate derivative, substituted quinol, or pharmaceutically acceptable salt, hydrate, or prodrug thereof, to a portion of an ACC enzyme in the *mycobacterium*. In certain embodiments, the portion of the ACC enzyme in the *mycobacterium* is the AccD6 subunit. This portion of the ACC enzyme has been shown to be necessary for pathogenicity in mycobacteria. By inhibiting this enzyme subunit, growth, cell wall lipid content, and cell morphology are disrupted. See Pawelczyk et al., *AccD6, a Key Carboxyltransferase Essential for Mycolic Acid Synthesis in Mycobacterium tuberculosis, Is Dispensable in a Nonpathogenic Strain*, J. BACTERIOL. 193(24):6960-6972 (2011).

In certain embodiments, the arylphenoxypropionate derivative, aryloxyphenoxyacetate derivative, aryloxyphenylacetate derivative, substituted quinol, or pharmaceutically acceptable salt, hydrate, or prodrug thereof, or combination thereof, disclosed herein can be used for inhibition of a Gram positive bacterium. In certain embodiments of the present disclosure, the Gram positive bacterium is a *mycobacterium*. The *mycobacterium* that undergoes inhibition may be any type of *mycobacterium*. It may, for instance, be a pathogenic *mycobacterium*. In certain embodiments, the *mycobacterium* belongs to a species selected from the group consisting of *Mycobacterium tuberculosis, Mycobacterium bovis, Mycobacterium africanum, Mycobacterium avium, Mycobacterium chelonae, Mycobacterium fortuitum, Mycobacterium intracellulare, Mycobacterium kansasii, Mycobacterium microti, Mycobacterium paratuberculosis, Mycobacterium leprae, Mycobacterium szulgai, Mycobacterium gordonae, Mycobacterium scrofulaceum, Mycobacterium lentiflavum, Mycobacterium peregrinum, Mycobacterium*

*marinum, Mycobacterium abscessus, Mycobacterium xenopi, Mycobacterium malmoense,* and *Mycobacterium shimoidei.*

The *mycobacterium* can be located in any region of the patient, such as the lung. The *mycobacterium* may be latent or active.

*Mycobacterium* present in a patient may be inhibited by delivering the composition to the patient. The mode of delivery may be selected based on a number of factors, including metabolism of the arylphenoxypropionate derivative, aryloxyphenoxyacetate derivative, aryloxyphenylacetate derivative, substituted quinol, or pharmaceutically acceptable salt, hydrate, or prodrug thereof, or combination thereof, the mode of administration of other drugs to the patient, the location and type of *mycobacterium* to be inhibited, the health of the patient, ability or inability to use particular dosing forms or schedules with the patient, preferred dosing schedule, and ease of administration. In specific embodiments, the mode of administration may be enteral, such as orally or by introduction into a feeding tube. In other specific embodiments, the mode of administration may be parenteral, such as intravenously or by inhalation.

The dosage amounts and administration schedule of the arylphenoxypropionate derivative, aryloxyphenoxyacetate derivative, aryloxyphenylacetate derivative, substituted quinol, or pharmaceutically acceptable salt, hydrate, or prodrug thereof, or combination thereof, can vary depending on other components of the composition and their effects on drug availability in a patient, the severity of infection, the intended schedule for administration, any drug toxicity concerns, and the patient's response to the drug. In certain embodiments, the amount and frequency of delivery may be such that levels in the patient remain well below levels at which toxicity to the patient becomes a concern. However the amount and frequency may also be such that the levels of the arylphenoxypropionate derivative, aryloxyphenoxyacetate derivative, aryloxyphenylacetate derivative, substituted quinol, or pharmaceutically acceptable salt, hydrate, or prodrug thereof, or combination thereof in the *mycobacterium* temporarily reach or continuously remain at a level sufficient to induce inhibition of the *mycobacterium*.

In certain embodiments, the administration of the arylphenoxypropionate derivative, aryloxyphenoxyacetate derivative, aryloxyphenylacetate derivative, substituted quinol, or pharmaceutically acceptable salt, hydrate, or prodrug thereof, or combination thereof, is calibrated to reach a threshold concentration in the plasma or tissue of a patient. Such calibration can take into consideration experimentally derived bioavailability, such as the exemplary study data provided below, as well as the mass of the patient. In certain embodiments, the threshold concentration is a proportion of the minimum inhibitory concentration ($MIC_{50}$). Representative $MIC_{50}$ data for certain arylphenoxypropionate derivatives are provided below.

In certain embodiments, and based on one or more of the considerations discussed, the unit dosage of the arylphenoxypropionate derivative, aryloxyphenoxyacetate derivative, aryloxyphenylacetate derivative, substituted quinol, or pharmaceutically acceptable salt, hydrate, or prodrug thereof, or combination thereof, is between about 1 mg/kg body weight to about 500 mg/kg body weight. In certain embodiments, the unit dosage is between about 5 mg/kg to about 350 mg/kg. In certain embodiments, the unit dosage is between about 10 mg/kg and about 200 mg/kg body weight.

In certain embodiments, the arylphenoxypropionate derivative, aryloxyphenoxyacetate derivative, aryloxyphenylacetate derivative, substituted quinol, or pharmaceutically acceptable salt, hydrate, or prodrug thereof, or combination thereof, has an $MIC_{50}$ value against *Mycobacterium tuberculosis* of about 0.1 µM to about 50 µM, or about 0.3 µM to about 20 µM, or about 0.35 µM to about 12.5 µM, or about 1 µM to about 10 µM, or about 1 µM to about 15 µM, or about 1 µM to about 25 µM.

The present disclosure further includes methods of identifying whether an arylphenoxypropionate derivative, aryloxyphenoxyacetate derivative, aryloxyphenylacetate derivative, substituted quinol, or pharmaceutically acceptable salt, hydrate, or prodrug thereof, or combination thereof, is able to inhibit a *mycobacterium*. Such methods include preparing or obtaining such a derivative, applying it to a *mycobacterium*, and identifying that the derivative inhibits the *mycobacterium*.

EXAMPLES

The following examples are provided to further illustrate certain embodiments of the disclosure. They are not intended to disclose or describe each and every aspect of the disclosure in complete detail and should be not be so interpreted. Unless otherwise specified, designations of cells lines and compositions are used consistently throughout these examples.

Example 1—Mtb AccD6 Protein Cloning, Expression, and Purification

A 1422 base pair DNA fragment containing the AccD6 gene (Rv2247) was amplified by PCR using Mtb H37Rv genomic DNA as a template (BEI Resources, Colorado State University). The following oligonucleotides were used as the forward and reverse primers, respectively: 5'-agatgaagc-catatgacaatcatggccccccgaggcggttg-3' (SEQ ID NO: 1) and 5'-agagtaagcttacagcgg gatgttcttgaggcggcc-3' (SEQ ID NO: 2).

The amplified DNA fragment was purified using the QIAquick PCR purification kit (Qiagen), following the manufacturer's protocol. The purified DNA fragment was digested with NdeI and HindIII, and then ligated using the corresponding restriction sites into a pET-28b vector (Novagen) to yield an N-terminal 6×(His) tag recombinant vector. BL21 star (DE3) cells were transformed with the AccD6::pET-28b vector. An overnight culture was diluted to 1:50 in fresh media and grown to mid-log phase at 37° C. in LB media (Difco).

The cells were induced with 1 mM (final concentration) IPTG and grown for 16 h at 16° C. Cells were harvested by centrifugation. The cell pellet was resuspended in 20 mM Tris-HCl pH 7.5, 10 mM imidazole, 0.5 M NaCl and 10% glycerol (v/v) containing 1 mM DNAse, 1 mM $MgCl_2$, and Complete™ EDTA-free protease inhibitor cocktail (Roche). The cell suspension was lysated using a French press at 18,000 psi and the resulting cell lysate was centrifuged at 15,000×g at 4° C. for 1 h. The supernatant was collected and filtered through a 0.2 µm filter and loaded onto a His-Trap nickel chelating column (GE Healthcare). (His)6-tagged AccD6 was eluted with a 0.2 L linear gradient of 75-500 mM imidazole in 20 mM Tris pH 7.5, 0.5 M NaCl, and 10% glycerol (v/v). The eluted protein was dialyzed overnight in a solution of 20 mM Tris pH 7.5, 50 mM NaCl, 10% glycerol (v/v), and 1 mM DTT. The purified protein was concentrated to 14 mg $mL^{-1}$ prior to crystallization. Size-exclusion chromatography confirmed that AccD6 is a two subunit oligomer in solution (data not shown).

Example 2—Mtb AccD6 Crystallization and Binding Analysis

Initial crystallization screening of Mtb AccD6 was performed via the sitting drop method using the Crystal Screen I and II, Index, SaltRx (Hampton Research), and Wizard I and II (Emerald Biosciences) screening kits. Crystals were grown by mixing 3 µL of protein solution with 2 µL of well solution and equilibrated by hanging-drop vapor diffusion at 295 K in 24-well Linbro trays containing 500 µL well solution. Crystals were obtained in 5-7 days. Apo AccD6 was crystallized in 60% tacsimate. The apo crystals were flash-cooled with Paratone N (Hampton Research, Laguna Niguel, Calif.) and the X-ray diffraction data were collected at the Advanced Photon Source beam line 23-ID using a MAR 300 CCD detector (MarMosaic from Marresearch-Charged Coupled Device). HKL2000 was used to integrate and scale the diffraction data. Examination of the diffraction data disclosed that the crystals were twinned in a pseudo-merohedral manner, and the correct space group was $P2_12_12_1$. The test for pseudo-merohedral twinning was accomplished using phenix.xtriage, and phenix.refine was used to refine twinned data with a twin law of k,h,−l. Diffraction images also exhibited anisotropy, ellipsoidal truncation and anisotropic scaling were performed on the data prior to refinement.

The structure of apo AccD6 was solved by molecular replacement as implemented in PHASER (University of Cambridge, UK). The complete PccB protein from *S. coelicolor* (PDB accession code: 1XNV) was used as a search model with water and ions removed.

For the formation of the AccD6 inhibitor complexes, haloxyfop-R was selected as a representative AccD6 inhibitor compound. Haloxyfop-R dissolved in DMSO as a 100 mM stock solution was added to the concentrated protein solution at a molar ratio of 5:1, and incubated for 1 h at 16° C. The haloxyfop-R complex was crystallized with 3.5 M sodium formate. Crystals were transferred directly to a cryoprotectant (30% ethylene glycol, Hampton Research) and flash-cooled in a liquid nitrogen stream at 100 K before data collection.

AccD6-haloxyfop-R diffraction data was collected at the Advanced Light Source Beamline 5.0.2 (Lawrence Berkeley National Laboratory, Berkeley, Calif.) with a Quantum 315 charge-coupled device detector. The HKL2000 program package was used for integration and scaling of the haloxyfop bound crystals. The AccD6 haloxyfop-R complex structure was solved by molecular replacement using PHASER with chain A of the apo AccD6 structure as a search model. All refinement was performed by PHENIX with intermittent manual model building done in COOT. Refinement statistics are summarized in Table 1. Geometry of the models was assessed with MOLPROBITY. All pictures were rendered with PyMol. Structures were deposited in the Protein Data Bank with the accession codes 4FB8 (for the apo structure) and 4G2R (for the haloxyfop-R bound structure).

The crystal structures of apo and haloxyfop-R bound Mtb AccD6 were determined at 3.0 and 2.3 Å resolution, respectively. Both structures show very good agreement with the X-ray diffraction data and excellent stereochemistry as provided in Table 1.

TABLE 2

Crystallographic statistics for the Mtb AccD6-Apo and haloxyfop-R complex structures.

| Data Collection | Apo | Haloxyfop-R |
|---|---|---|
| Space Group | $P2_12_12_1$ | I222 |
| Resolution | 50-3.0 | 63-2.3 |
| Twin Fraction | 0.48 | NA |
| Unit Cell a, b, c (Å) | 82.3 × 82.4 × 157.9 | 117.8 × 126.2 × 161.7 |
| Redundancy | 11.9 (8.7) | 7.0 (6.3) |
| Observations | 20652 | 54918 |
| Observations Test Set | 1096 | 1996 |
| Completeness (%) | 97.8 (90.4) | 100 (99.0) |
| $R_{merge}$ | 15.2 (88.1) | 7.80 (3.90) |
| $R_{pim}$ | 0.02 (0.11) | 0.01 (0.14) |
| I/Iσ | 29.5 (2.83) | 12.9 (2.70) |
| Refinement | | |
| $R_{work}$ | 23.7 | 16.6 |
| $R_{free}$ | 30.4 | 19.8 |
| Number of Atoms | | |
| Protein | 6221 | 6483 |
| Solvent | 5 | 552 |
| Ligand (including ions) | 0 | 95 |
| Ramachandran analysis | | |
| Most favorable + allowed (%) | 95.9 | 99.8 |
| Root mean square deviation | | |
| Bond Lengths (Å) | 0.008 | 0.007 |
| Bond Angles (o) | 1.227 | 1.118 |

Figure 1B:
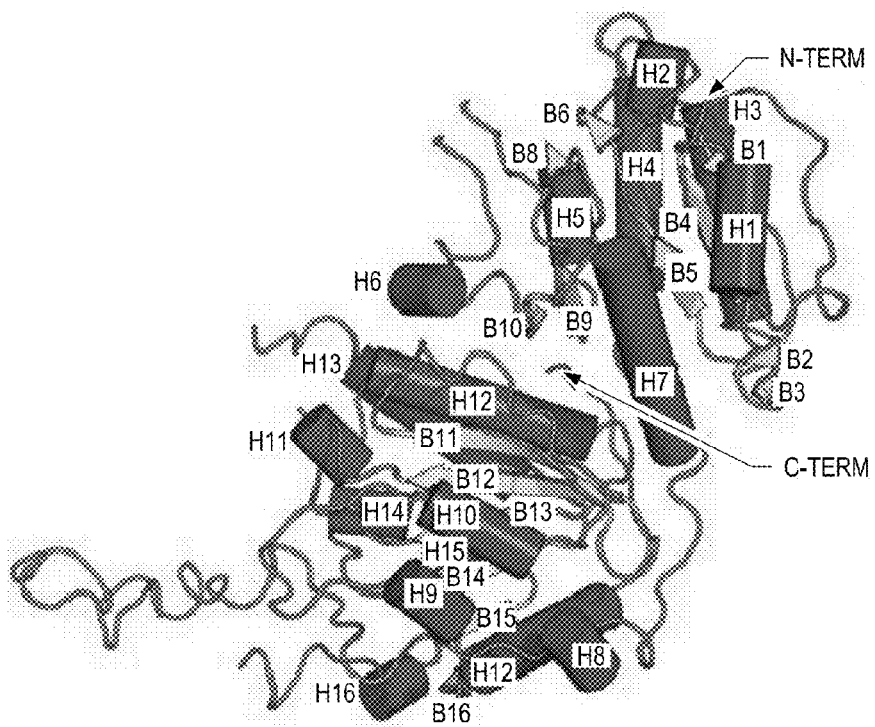
FIG. 1B illustrates schematically the crystal structure of a single Mtb AccD6 apo subunit.
Figure 1C:
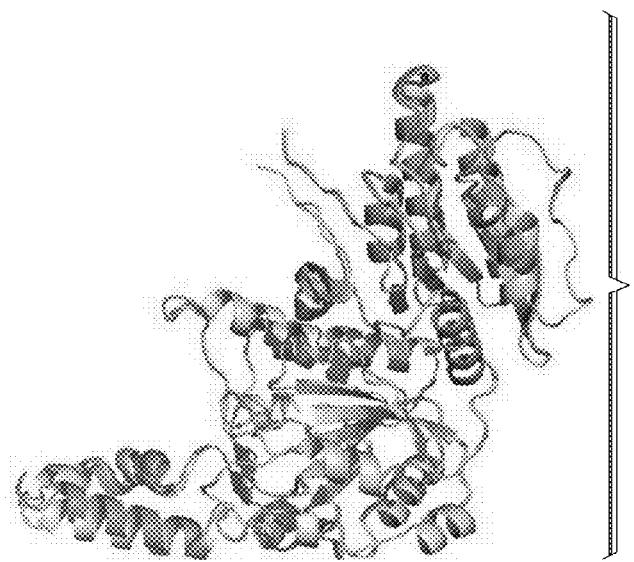
FIG. 1C illustrates schematically the superimposed crystal structures of the first and second Mtb AccD6 apo subunits.
Figure 3A:
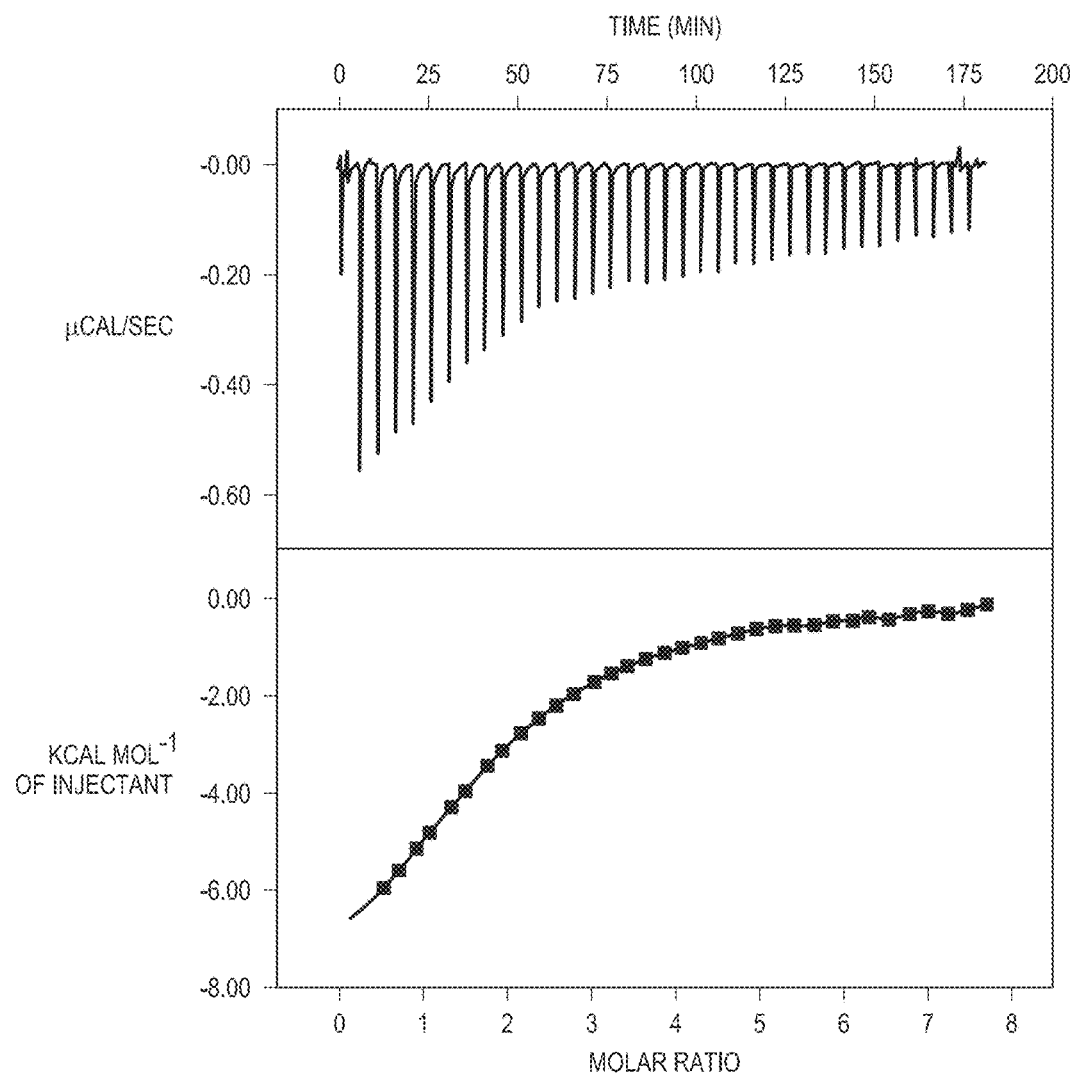
FIG. 3A is a plot of haloxyfop-R binding to Mtb AccD6.
Figure 3B:
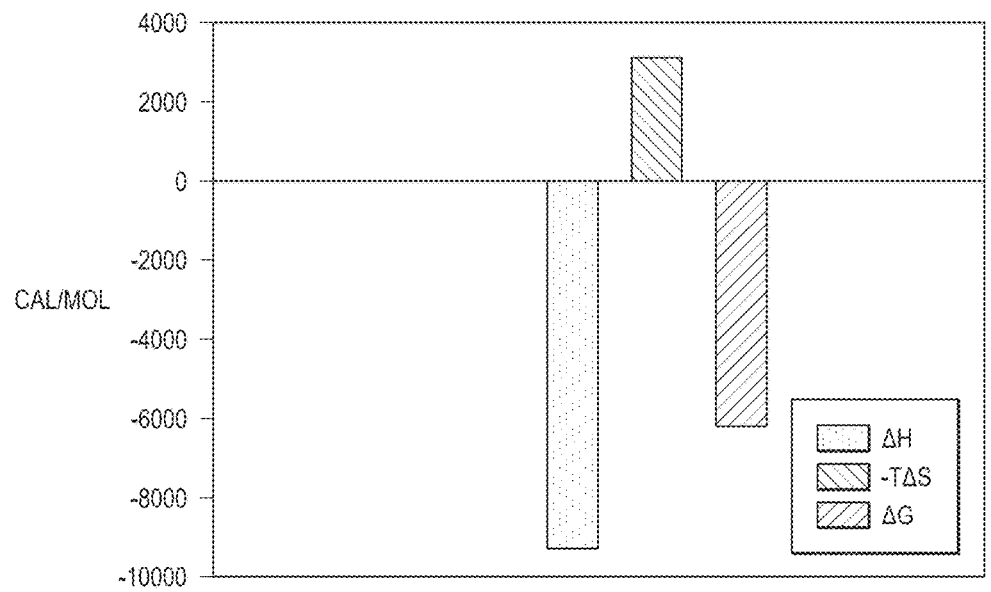
FIG. 3B is a graph of the thermodynamic discrimination profile of haloxyfop-R binding to Mtb AccD6.

Mtb AccD6 is a dimer of identical subunits, each comprising 473 amino acids, differing from what was initially proposed that all Mtb AccD homologues would adopt a hexameric quaternary assembly. The protein forms a mixed α/β fold with a total of 17 α-helices and 16 β-strands that resemble the crotonase superfamily fold. The crystal structure of apo Mtb AccD6 is illustrated at FIG. 1A as a ribbon diagram colored by secondary structure. The crystal structure of haloxyfop-R bound Mtb AccD6 is illustrated at FIG. 1B. The haloxyfop ligands are depicted as sticks and balls, and the AccD6 subunits are depicted by differences in color, both colored by secondary structure. Subunit 1 is colored red, yellow, and green, subunit 2 is colored cyan, purple, and beige. The protein forms a mixed α/β fold with a total of 17 α-helices and 16 β-strands that resemble the crotonase superfamily fold. Unlike the hexameric ring-shaped architecture found in the structure of AccD5 from Mtb, AccD6 is a homodimer like the yeast and *E. coli* ACC CT domains. Superimposition of the two subunits show a RMSD (root mean square deviation) value of 1.0 Å (calculation performed using the Cα atoms of 411 residues) as seen in FIG. 1C. The total surface area for the two subunit complex is 32,370 Å$^2$, with a buried surface area of 5,260 Å$^2$ at the subunit interface. Each subunit of the dimer consists of two domains: the N-terminal domain (α-helices 1-7 and β-strands 1-10) and the C-terminal domain (helices 8-17 and β-strands 11-16). H4 and H5 of the N-terminal domain of one subunit and H13 and H14 of the C-terminal domain of the second subunit (FIG. 3A) interact at the dimer interface.

The active sites of the Mtb AccD6 enzyme were modeled by superposition of the Mtb AccD6 apo structure with the previously reported β-subunit of ACC from *S. coelicolor* in complex with acetyl-CoA. The Mtb AccD6 active site is formed by the dimer interface as shown in FIG. 1A. The entrance to the active site is an opening measuring approximately 8 Å by 14 Å on the surface, and it leads to a cavity of approximately 400 Å³. The cavity defined by H2, H5, H14, as well as the loop between 1315 and H16, expands to allow substrate binding. In the active site of other species such as the *S. coelicolor* ACC, the key catalytic residue consists of two pairs of oxyanion-stabilizing residues (the oxyanion holes). Gly419 and Ala420 hydrogen bond with the carbonyl group of biotin, whereas Gly182 and Gly183 hydrogen bond with the carbonyl group of acetyl-CoA. These four residues are highly conserved among the CT domains of different species including Mtb AccD6 (Gly336, Ala367, Gly137, and Gly138). The adenine and phosphate moieties of acetyl-CoA are apparently exposed to solvent, where they make contact with the surface of the protein, while the acyl portion inserts into the cavity of the protein. The adenine moiety of acetyl-CoA lies next to the loop preceding β-strand 15 and the loop preceding H4 and H2 from the adjacent subunit. The adenine $NH_2$ extension is poised to hydrogen bond with the backbone oxygen of Ala99, while the adenine N7 atom is in position to hydrogen bond with Met64. The phosphate oxygen atoms of acetyl-CoA are positioned to form electrostatic interactions with Lys401, Lys403, and Lys404. The terminal carbonyl oxygen atom fits into an oxyanion hole composed of the backbone nitrogen atom of Gly131 and the nitrogen atom of the ring of the biotin molecule. The biotin cofactor lies deeper in the cavity next to the CoA-acyl chain and is largely buried.

Figure 2A:
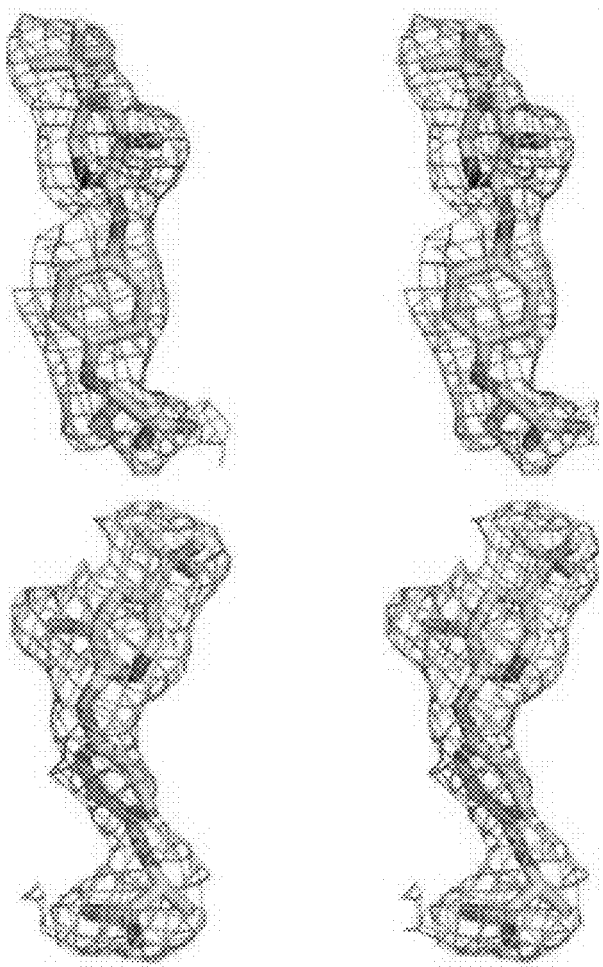
FIG. 2A illustrates schematically the electron density of haloxyfop ligands.
Figure 2B:
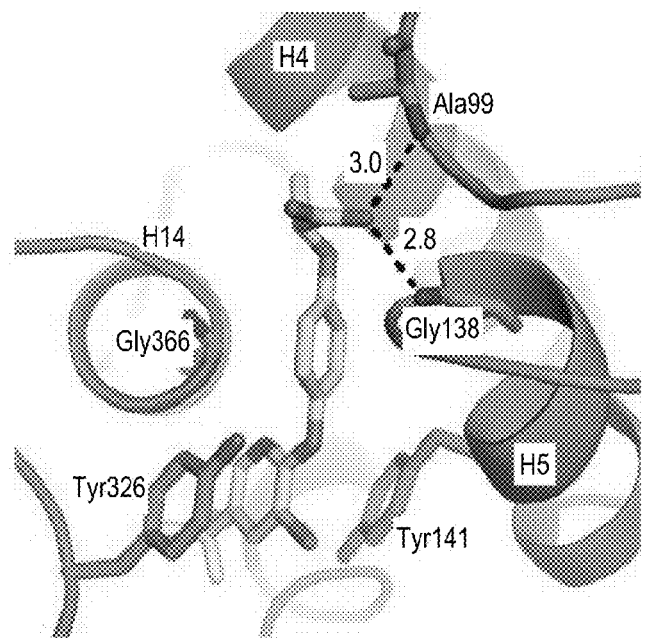
FIG. 2B illustrates schematically the interaction of haloxyfop with the first Mtb AccD6 binding site.
Figure 2C:
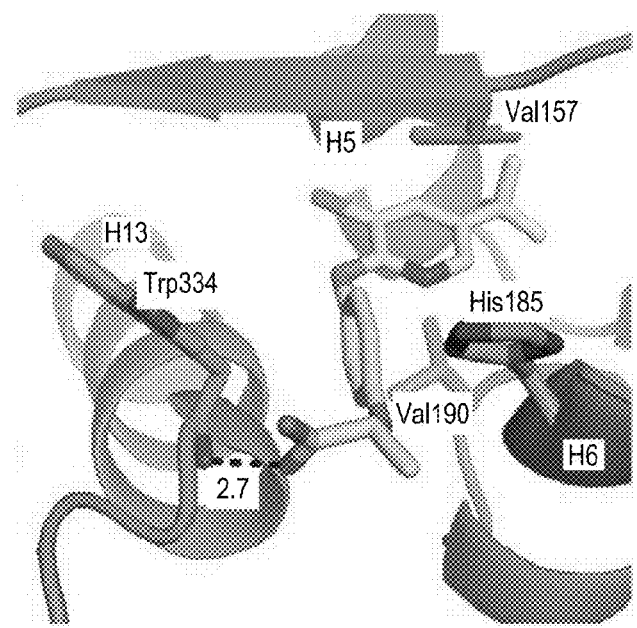
FIG. 2C illustrates schematically the interaction of haloxyfop with the second Mtb AccD6 binding site.

The crystal structure of AccD6 co-crystallized with haloxyfop-R shows two molecules bound per subunit. Both subunits of the haloxyfop-bound dimer in the asymmetric unit bear high similarity with a RMSD value of 0.7 Å (over 438 Cα atoms). Electron density of the haloxyfop ligands is shown in FIG. 2A, with composite OMIT map electron density (blue contoured at 1σ) shown in wall eye stereo. The first and second haloxyfop binding sites are illustrated at FIGS. 2B and 2C, with the ligand illustrated in yellow and the protein illustrated in green, and wherein dashes indicate hydrogen bonding and numbers represent distances in A. Both haloxyfop-R binding clefts are located at the subunit interface, contacting both. The first binding site (designated site 1) locates in a cleft that partially overlaps with the active site (FIG. 2B). The second binding site (site 2) binds in a cleft (FIG. 2C), connected to binding site 1 by a small channel of approximately 6 Å in diameter and 5 Å in length.

Site 1 is formed by three helices: encompassing H13, H14, and H5' (prime designates the other subunit in the dimer). In site 1, the carboxyl end of haloxyfop is solvent exposed, while the tri-fluoromethylpyridyl is buried deeper to allow hydrophobic contacts. The tri-fluoromethylpyridyl is held in place by base stacking between the aromatic side chains of Tyr141 and Tyr326. The phenyl ring in the center position of haloxyfop makes van der Waals contacts with Gly366 and Gly137, while the tri-fluoromethyl group makes hydrophobic interactions with Tyr320. In site 1, the carboxylate group of haloxyfop forms hydrogen bonds with the backbone amide of Gly138 (2.8 Å) and Ala99 (3 Å), FIG. 2B. Site 2 (FIG. 2C) is formed by the C-terminal region of H13, H6', the N-terminal loop of H6', the C-terminal loop to β-strand 9, and H5'. This site is similar to site 1 in that it contains a solvent exposed carboxyl group and a tri-fluoromethylpyridyl ring that buries deeper into the hydrophobic environment of the protein. The tri-fluoromethylpyridyl ring forms hydrophobic contacts with Val157. The phenyl ring in the center of haloxyfop makes contacts with Trp334, Val190, and Ser188. In site 2, haloxyfop only makes one hydrogen bond: the carboxyl group to the amide backbone of Trp334 (2.7 Å). The methyl group is positioned to make hydrophobic contacts with His 185. The apo structure and the haloxyfop bound structure share a global similarity, with the differences between the structures centralized to the residues and secondary structural elements surrounding both binding sites.

Superimposition between the apo and haloxyfop bound structures reveals a RMSD value of 1.0 Å (performed over 832 Cα residues) as seen in FIG. 1C. At site 1 (FIG. 2B), both Tyr141 and Tyr326 adopt different rotamer conformations to accommodate the stacking interactions with haloxyfop. In comparison with the apo structure, the phenyl ring in the center of haloxyfop in site 1 forces H5 outward (approximately 1.5 Å), while the carboxyl group of haloxyfop in site 1 forces the loop between 136 and H4 (bearing residue Ala99) outward by 1.1 Å. In contrast, the haloxyfop in site 2, by means of the phenyl ring in the center, displaces H6 by 2.1 Å. Both rings of haloxyfop at site 2 shift the loop between 39 and H5 (bearing residue 157) outward in comparison to the apo structure (approximately 1.3 Å). The tri-fluoromethyl group of haloxyfop at site 2 is located near Met151, which forms a different rotamer conformation than the apo structure, and 39 also shifts approximately 1.3 Å. The flexibility of these residues and secondary structural elements allow the formation of site 2 in the Mtb structure.

Example 3—In Vitro Mtb AccD6 Inhibition Assay

AccD6 activity was monitored by measuring the reduction of $NAD^+$ dependent of the synthesis of acetyl-CoA, in an assay coupled to citrate synthase-malate dehydrogenase reaction. The formation of NADH, which is proportional to the activity of Mtb ACCD6, was measured spectrophotometrically at 340 nm.

The reaction catalyzed by AccD6 proceeds in two steps. In the first step, biotin bound to a biotin carboxylase carrier protein (BCCP) is carboxylated by biotin carboxylase. Subsequently, AccD6 catalyzes the transfer of the carboxyl moiety to an acetyl-CoA molecule to form malonyl-CoA. The reaction is illustrated schematically below:

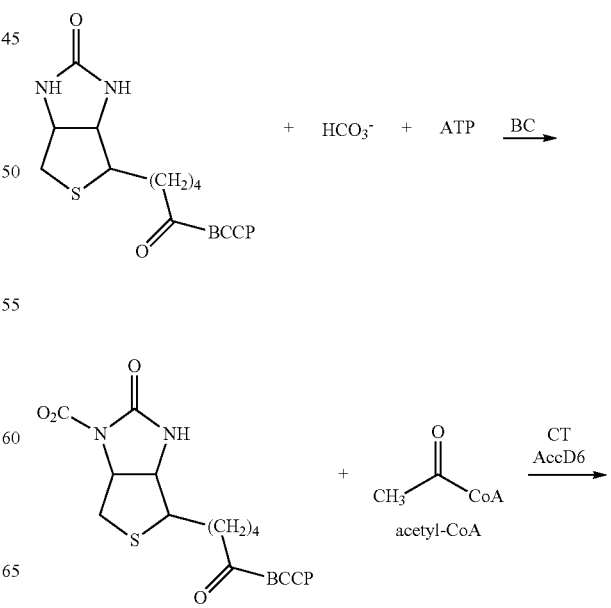

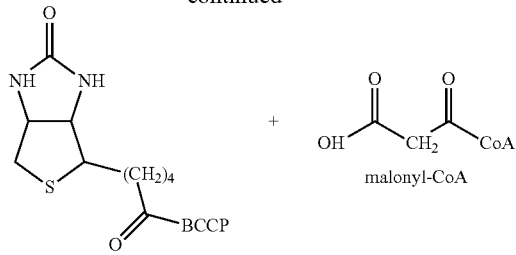

-continued malonyl-CoA

AccD6 activity was monitored by measurement of the reverse reaction rate of the reaction catalyzed by the enzyme. Using malonyl-CoA as a substrate, the formation of acetyl-CoA was coupled to the citrate synthase-malate dehydrogenase reaction involving the reduction of $NAD^+$ (25). This is in accordance to the coupled reactions:

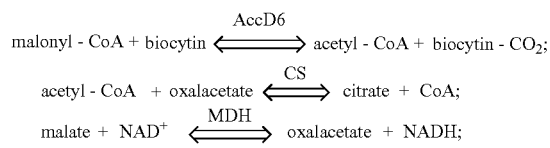

$$\text{malonyl-CoA} + \text{biocytin} \xleftrightarrow{\text{AccD6}} \text{acetyl-CoA} + \text{biocytin-}CO_2;$$

$$\text{acetyl-CoA} + \text{oxalacetate} \xleftrightarrow{\text{CS}} \text{citrate} + \text{CoA};$$

$$\text{malate} + NAD^+ \xleftrightarrow{\text{MDH}} \text{oxalacetate} + \text{NADH};$$

where CS and MDH correspond, respectively, to citrate synthase and malate dehydrogenase. The formation of NADH, which is proportional to the activity of Mtb AccD6, was measured spectrophotometrically at 340 nm using a Thermo Scientific Multiscan Go Plate Reader. The MDH reaction was initially kept in equilibrium in the absence of AccD6. Addition of AccD6 to the reaction mix, in the presence of CS, induces oxalacetate consumption by CS and equilibrium shift of the MDH reaction, leading to the AccD6-dependent formation of NADH. The reaction, which was carried out in a Corning 384-well plate at 30° C., was monitored for 30 minutes. The 100 μL reaction contained 0.6 mg $mL^{-1}$ BSA, 100 mM potassium phosphate pH 8.0, 20 mM L-malic acid, 0.5 mM $NAD^+$, 6 mM biocytin, 3.6 U $mL^{-1}$ MDH, 6.8 U $mL^{-1}$ CS, and varied concentrations of malonyl CoA (0 to 40 μM). The kinetic parameters were calculated at an enzyme concentration of 2 μM and 1% (v/v) DMSO. Data was fit to the Henri-Michaelis-Menten Equation (HMM):

$$v=V_{max}[S]/K_m+[S]$$

in which v, $V_{max}$, [S], and $K_m$ correspond to, respectively, the steady-state reaction rate, the maximum reaction rate, substrate concentration, and the HMM constant for substrate S; using the GraphPad Prism demo version for Windows (GraphPad Software, La Jolla Calif. USA). The $K_m$ for malonyl-CoA was calculated to be 390±70 μM, and $V_{max}$ 5.5±0.4 μM $min^{-1}$.

Enzymatic inhibition by representative arylphenoxypropionate derivatives, aryloxyphenoxyacetate derivatives, aryloxyphenylacetate derivatives, and substituted quinols was tested by repeating the protocol above in the presence of malonyl-CoA and either 300 μM or 200 μM of the test inhibitor. The concentration of the test inhibitors required to reduce the Mtb AccD6 activity to half of its initial value in the absence of inhibitor ($IC_{50}$) was assigned by the addition of 1 μL of 100× inhibitor stock to a 100 μL reaction. 1 μL DMSO was added to the control reactions (enzyme activity in absence of inhibitor). The reaction was incubated at room temperature for 20 minutes and was initiated by the addition of 300 μM malonyl-CoA, in the presence of concentrations of the test inhibitor from 10 μM to 2000 μM. The dose response was measured by calculating the decrease in initial velocity, and $IC_{50}$ values were assigned according to Equation (2):

$$v_i/v_o=1/[1+([I]/IC_{50})^n] \quad (2)$$

where $v_i/v_o$, [I], and n correspond to, respectively, enzyme fractional activity in presence of inhibitor I, inhibitor concentration, and the Hill's coefficient. The $IC_{50}$ values for the representative compounds are provided in Table 3 below.

Preliminary studies of commercially available herbicides indicated that of clodinofop, cyhalofop, haloxyfop, fluazifop, and diclofop (from the fop family); and sethoxydim, alloxydim, cycloxydim, tepraloxydim, and tralkoxydim (from the dim family), only haloxyfop exhibited Mtb AccD6 inhibition, and none exhibited whole *Mycobacterium tuberculosis* cell inhibition.

Example 4—Isothermal Titration Calorimetry (ITC)

The binding of haloxyfop-R to Mtb AccD6 was further characterized by ITC measurements to determine the stoichiometry of interaction (n) and the dissociation constant ($K_d$). The ITC plot obtained from titration of haloxyfop-R is displayed in FIG. 3A. Data was best fitted to the single mode data analysis option giving an n value of 1.83±0.03 and a molar ratio of 2:1. The n value suggests that two molecules of haloxyfop-R bind per subunit, consistent with the presence of two haloxyfop-R binding sites per subunit observed in the crystal structure. The $K_d$ value of 35.84±1.38 μM is in good agreement with the kinetically determined $IC_{50}$. These results are indicative of the presence of two binding sites on each subunit.

The thermodynamic discrimination profile for haloxyfop binding (ΔH=−9300 cal/mol; −TΔS=3122 cal/mol/degree; ΔG=−6177 cal/mol) is illustrated at FIG. 3B, and is plotted as a single binding event, as explained above. The profile indicates that its interaction with AccD6 is mostly enthalpic driven (due to hydrogen bond donors and acceptors good placement on both binding sites, as well as due to favorable van der Waals interactions), and presents unfavorable entropy (due to haloxyfop flexibility and high polarity).

Example 5—In Vitro Mtb Inhibition Assay

A whole-cell assay was used to evaluate growth inhibition of the Mtb strain $mc^2$-7000 by each of the arylphenoxypropionate derivatives of the table below. The inhibitory activity against Mtb whole cells was evaluated against $MC^2$-7000 strain cultures (10 mL Difco 7H9, 100 μL dextrose, 1 mL OADC, 85 μL NaCl (10% solution), 25 μL Tween 80, 10 μL of Malachite Green (0.25 mg/mL), and 1 mM pantothenic acid), grown for 3 days, and diluted to $OD_{600}$ 0.005. Each compound was tested over a range from 100 μM-100 nM. After 6 days of incubation at 37° C., culture plates were stained with resazurin and read on the $7^{th}$ day. The $IC_{50}$ and MIC for the representative arylphenoxypropionate derivatives is provided in Table 2. These values are comparable to those of currently employed tuberculosis drugs, which have MIC values in the low micromolar range.

TABLE 3

IC$_{50}$ and MIC for Arylphenoxypropionate Derivatives for Mtb Strain mc$^2$-7000

| Compound | IC$_{50}$ (μM) | MIC (μM) |
|---|---|---|
| fenoxaprop-p | 1.5 | 25 |
| fenoxaprop-p-ethyl | N/A | 1.56 |
| haloxyfop-p | 21.4 | N/A |
| NZ-246 | N/A | 3 |
| NZ-247 | 2.5 | N/A |
| NZ-250 | N/A | 3.12 |
| NZ-251 | N/A | 0.23 |
| NZ-252 | Not Soluble | Not Soluble |
| NZ-253 | >15 | N/A |
| NZ-254 | >15 | N/A |
| NZ-255 | 1.2 | N/A |
| NZ-256 | N/A | 1.5 |
| NZ-257 | 1.5-1.9 | N/A |
| NZ-258 | 2.1-3.1 | 50 |
| NZ-259 | 1.6-2.6 | >50 |
| NZ-260 | N/A | 0.19-2.3 |
| NZ-261 | 1.8 | N/A |
| NZ-262 | 1.8 | >25 |
| NZ-263 | 7.8 | >50 |
| NZ-264 | 3.4 | >12.5 |
| NZ-265 | 0.57 | 3 |
| NZ-266 | 0.99 | >12.5 |
| NZ-267 | 2.4 | >25 |
| NZ-268 | 1.7 | >12.5 |
| NZ-269 | 15.8 | >50 |
| NZ-270 | 9.7 | >50 |
| NZ-271 | 11.6 | >50 |
| NZ-272 | 5.8 | >12.5 |
| NZ-273 | 7.9 | >25 |
| NZ-274 | 3.7 | 0.173 |
| NZ-275 | 3.8 | 12.5 |
| NZ-276 | 7.3 | 3.1 |
| NZ-277 | 5.6 | 12.5 |
| NZ-278 | 1.1 | 3.1 |
| NZ-279 | 0.8 | >50 |
| NZ-280 | 50% inhibition at 20 uM | 6 |
| NZ-281 | 30% inhibition at 20 uM | 50 |
| NZ-282 | 40% inhibition at 20 uM | Not Active |
| NZ-283 | 33% inhibition at 20 uM | 12 |
| NZ-284 | 17 | 4.5 |
| NZ-285 | Not Active | 12 |
| NZ-286 | 1.4 | 3 |
| NZ-287 | 0.52 | 12 |
| NZ-288 | 12 | 25 |
| NZ-289 | 6.1 | 0.35 |
| NZ-290 | 2.5 | 1.5 |
| NZ-291 | 30% inhibition at 20 uM | 25 |
| NZ-292 | 42% inhibition at 20 uM | 12 |
| NZ-293 | 1 | 3 |
| NZ-294 | 12.5 | 3 |
| NZ-295 | 0.93 | 4.5 |
| NZ-296 | 1.8 | 3 |
| NZ-297 | 10 | 12 |
| NZ-298 | 0.28 | 25 |
| NZ-299 | 0.324 | 12 |
| NZ-300 | 0.82 | 7.5 |
| NZ-301 | 0.265 | 12 |
| NZ-302 | 50% inhibition at 20 uM | 3 |
| NZ-303 | 50% inhibition at 20 uM | 4.5 |
| NZ-304 | 3.4 | 25 |
| NZ-305 | 50% inhibition at 15 uM | 3 |
| NZ-306 | 4.6 | 25 |
| NZ-307 | 2.5 | 3 |
| NZ-308 | 8 | 4.5 |
| NZ-309 | 0.172 | 12 |
| NZ-310 | 0.182 | 6 |
| NZ-311 | 10 | 3 |
| NZ-312 | 0.26 | 6 |
| NZ-313 | 0.32 (racemic mixture) | 0.38 |
| NZ-314 | 17.5 | 6 |
| NZ-315 | 1.7 | 25 |
| NZ-316 | 15 | 6 |
| NZ-317 | 15 | 6 |
| NZ-318 | 1.5 | 12 |
| NZ-319 | 20 | 6 |
| NZ-320 | 20 | 50 |
| NZ-321 | 20 | 50 |
| NZ-322 | 0.092 | 12 |
| NZ-323 | 3.6 | 6 |
| NZ-325 | 0.63 | 3 |
| NZ-326 | 2.5-4.4 | 3 |
| NZ-327 | 0.3 | 12 |
| NZ-328 | 10 | 12 |
| NZ-329 | 0.37 | 12 |
| NZ-330 | 0.24 (racemic mixture) | 1.5 |
| NZ-331 | 0.8 | 0.8 |
| NZ-332 | 0.65 | 0.8 |
| NZ-333 | 12.5 | 12 |
| NZ-334 | 10 | 25 |
| NZ-335 | 15 | 12 |
| NZ-336 | 15 | 12 |
| NZ-337 | 2.3 | 25 |
| NZ-338 | 7.2 | 25 |
| NZ-341 | 2.6 | 12 |
| NZ-342 | 0.6 | 50 |
| NZ-343 | 0.4 | 25 |
| NZ-344 | 4.1 | 25 |
| NZ-345 | 0.5 | 25 |
| NZ-346 | 0.4 | 50 |
| NZ-347 | Not Active | 15 |
| NZ-348 | Not Active | 2 |
| NZ-349 | 7 | 8 |
| NZ-350 | 1.6 | Not Active |
| NZ-351 | Not Active | Not Active |
| NZ-352 | Not Active | 1.5 |
| NZ-353 | 4 | Not Active |
| NZ-354 | 7.3 | 1 |
| NZ-355 | 20 | 4.5 |
| NZ-356 | 1.7 | 25 |
| NZ-357 | 3.6 | 20 |
| NZ-358 | 20 | 5.8 |
| NZ-359 | 8.4 | >50 |
| NZ-360 | 13.3 | 4.3 |
| NZ-361 | 19% inhibition at 20 uM | 3.2 |
| NZ-362 | 20% inhibition at 20 uM | 6.5 |
| NZ-363 | 4.7 | >50 |
| NZ-364 | 20% inhibition at 20 uM | 1.34 |
| NZ-365 | 6.2 | 18.88 |
| NZ-366 | 4.9 | 0.56 |
| NZ-368 | 3.6 | 2.07 |
| NZ-369 | 0.87 | 0.73-0.98 |
| NZ-370 | 1 | 1.8 |
| NZ-371 | 0.86 | 19.97 |
| NZ-372 | 2.75 | 4.67 |
| NZ-373 | 1.66 | Not Active |
| NZ-374 | Not Active | Not Active |
| NZ-376 | 0.874 | Not Active |
| NZ-377 | 7.9 | Not Active |
| NZ-378 | Not Active | 2.2 |
| NZ-379 | Not Active | Not Active |
| NZ-380 | Not Active | 3.4 |
| NZ-381 | Not Active | 7.3 |
| NZ-382 | 0.27-0.35 | Not Active |
| NZ-383 | 0.8-1.17 | 3.9 |
| NZ-385 | 0.87 | 3 |
| NZ-386 | 0.62 | 1.1-2.1 |
| NZ-387 | 0.26 | 2.7-8 |
| NZ-388 | 3 | 2.1 |
| NZ-389 | 0.21 | 1.2-2.2 |
| NZ-390 | 15.4 | Not Active |
| NZ-391 | Not Active | Not Active |
| NZ-392 | 7.18 | 7.28 |
| NZ-393 | 5.07 | ND |
| NZ-394 | 0.98 | Not active |
| NZ-395 | 0.16 | 0.6-0.9 |
| NZ-396 | 11.35 | 6.19-8.6 |
| NZ-397 | 0.45 | Not Active |
| NZ-398 | 3.6 | 0.89 |
| NZ-399 | 0.18 | 1.36 |
| NZ-400 | 0.21 | 0.61 |

TABLE 3-continued

IC$_{50}$ and MIC for Arylphenoxypropionate Derivatives for Mtb Strain mc$^2$-7000

| Compound | IC$_{50}$ (μM) | MIC (μM) |
| --- | --- | --- |
| NZ-401 | 0.12 | 0.54 |
| NZ-402 | 0.21 | 2.16 |
| NZ-403 | 0.16 | 1.24 |
| NZ-404 | 14.36 | 38% at 50 uM |
| NZ-405 | 0.15 | 17.5 |
| NZ-406 | Not Active | 46% at 50 uM |
| NZ-407 | 0.11 | 11.7 |
| NZ-408 | 0.21 | 6.5 |
| NZ-409 | 0.66 | N/A |
| NZ-410 | 0.38 | N/A |
| NZ-411 | 0.24 | N/A |
| NZ-412 | 17% at 20 uM | ND |
| NZ-413 | 14 | ND |
| NZ-414 | 15 | ND |
| NZ-415 | 20 | ND |
| NZ-416 | 20% at 20 uM | ND |
| NZ-417 | 10% at 20 uM | ND |
| propaquizafop | 2.1 | 1.56 |
| quizalofop-p | 0.8 | N/A |
| quizalofop-p-ethyl | 2.3 | 0.68-1.56 |
| WUXI-N4 | No inhibition at 20 uM | ND |
| WUXI-N5 | No inhibition at 20 uM | ND |
| WuXi-N6 | 11% inhibition at 20 uM- pH 8.0/17% inhibition at 20 uM- pH 8.5 | ND |
| WuXi-N7 | 18% at 20 uM | ND |
| WuXi-N8 | 40% inhibition at 20 uM- pH 8.0/47% inhibition at 20 uM- pH 8.5 | ND |

Example 6—In Vivo Protein Plasma Binding Assays of Arylphenoxypropionate Derivatives Protein plasma binding assays were conducted in female mice for each of the arylphenoxypropionate derivatives quizalofop-p, quizalofop-p-ethyl, fenoxaprop-p, and fenoxaprop-p-ethyl.

Results are summarized in Table 3 below. Due to plasma esterase activity, quizalofop-p-ethyl and fenoxaprop-p-ethyl were not stable under assay conditions, and the carboxylic acid equivalents were quantified instead.

TABLE 4

Plasma Protein Binding Assay Data for Representative Arylphenoxypropionate Derivatives

| Compound | Percentage of Compound Bound | Percentage of Compound Recovered |
| --- | --- | --- |
| quizalofop-p | 96.8% | 90% |
| fenoxyfop-p | 98.58% | 76% |

Example 7—In Vivo Pharmacokinetic Studies

Quizalofop-p-ethyl or quizalofop-p dissolved in carboxymethylcellulose or canola oil was administered by gavage to mice at a dosage of 50 mg/kg. For each of the four treatment groups, blood was harvested from each mouse at 1, 2, 4, and 6 hours after gavage, and a final blood sample was withdrawn from the mice at 8, 24, 48 or 72 hours after gavage.

For each blood sample withdrawn, 50 μL of plasma was isolated for methanol extraction of quizalofop-p and quizalofop-p-ethyl. These samples were analyzed by liquid chromatography in a Bruker micrOTOF Q-II LC/MS. Samples were quantified using standard calibration curves for both quizalofop-p and quizalofop-p-ethyl by addition of a known concentration of each compound to 50 μL of mouse plasma.

Both quizalofop-p and quizalofop-p-ethyl were detected in samples. The concentration of quizalofop-p-ethyl detected at all collection timepoints was much lower than the concentration of quizalofop-p detected. The peak plasma concentration of quizalofop-p of 35 L/mg was detected in blood samples harvested 8 hours after gavage.

NZ-331 dissolved in polyethylene glycol (PEG) or canola oil was administered by gavage to mice at a dosage of 100 mg/kg. Blood was harvested from each mouse at 30 minutes after gavage and a final sample was withdrawn from the mice at 90 minutes after gavage. For each blood sample withdrawn, 50 μL of plasma was isolated for methanol extraction of NZ-331. These samples were analyzed by liquid chromatography in a Bruker micrOTOF Q-II LC/MS. Samples were quantified using standard calibration curves for NZ-331 by addition of a known concentration of the compound to 50 μL of mouse plasma.

Figure 4:
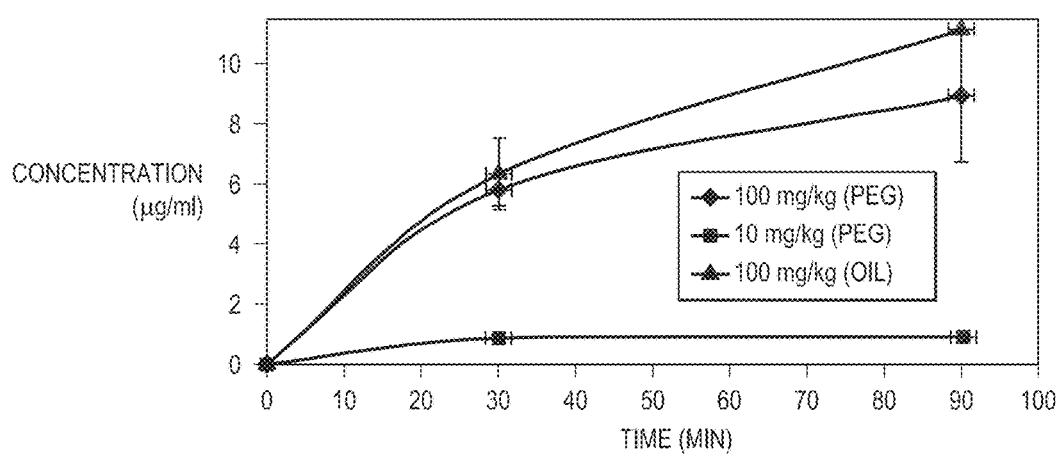
FIG. 4 illustrates the plasma concentration of NZ-331 in blood samples collected from mice following administration of NZ-331 dissolved in canola oil by gavage at a dosage of 100 mg/kg.

FIG. 4 illustrates the plasma concentration of NZ-331 in blood samples collected from mice following administration of NZ-331 dissolved in polyethylene glycol (PEG) or canola oil by gavage at a dosage of 100 mg/kg. NZ-331 was detected in the samples. The peak plasma concentration of NZ-331 detected in blood samples harvested 30 minutes after gavage was approximately 6 μL/mg and the peak plasma concentration of NZ-331 detected in blood samples harvested 90 minutes after gavage was 9 μL/mg.

NZ-332 dissolved in polyethylene glycol (PEG) or canola oil was administered by gavage to mice at a dosage of 100 mg/kg. Blood was harvested from each mouse at 30 minutes after gavage and a final sample was withdrawn from the mice at 90 minutes after gavage. For each blood sample withdrawn, 50 μL of plasma was isolated for methanol extraction of NZ-331. These samples were analyzed by liquid chromatography in a Bruker micrOTOF Q-II LC/MS. Samples were quantified using standard calibration curves for NZ-331 by addition of a known concentration of the compound to 50 μL of mouse plasma.

Figure 5:
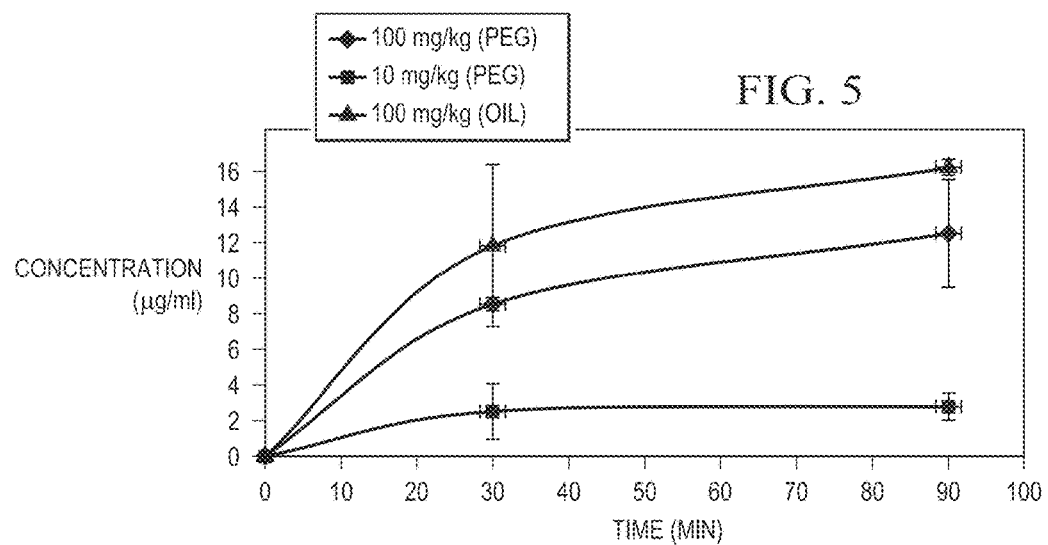
FIG. 5 illustrates the plasma concentration of NZ-332 in blood samples collected from mice following administration of NZ-332 dissolved in canola oil by gavage at a dosage of 100 mg/kg.

FIG. 5 illustrates the plasma concentration of NZ-332 in blood samples collected from mice following administration of NZ-332 dissolved in polyethylene glycol (PEG) or canola oil by gavage at a dosage of 100 mg/kg. NZ-332 was detected in the samples. The peak plasma concentration of NZ-332 detected in blood samples harvested 30 minutes after gavage was approximately 9 μL/mg and the peak plasma concentration of NZ-332 detected in blood samples harvested 90 minutes after gavage was 13 μL/mg.

NZ-331 and NZ-332 dissolved in canola oil was administered by gavage to mice at a dosage of 200 mg/kg. The first treatment group received only a single dose. The second and third treatment groups received two doses administered 8 hours apart. Blood was harvested from the mice at 1, 2, and 4 hours after gavage, and a final sample was withdrawn from the mice at 8, 12, and 24 hours after gavage. Table 4 includes dosage and blood sample harvest data for this group of mice.

TABLE 4

NZ-331 and NZ-332 dissolved in canola oil was administered by gavage to mice at a dosage of 200 mg/kg
Maximum tolerated dose: Two doses (8 h apart), 200 mg/Kg, oil, gavage

|  | Mouse | Dose | time of dose | Survival | Terminal |
|---|---|---|---|---|---|
| First dose at t = 0 | 1 | 200 mg/kg; 200 ul of 20 mg/ml | 0 (9:00 am) | 1 (10:00 am) | 8 (5:00 pm) |
| Bleed at t = 1 hour | 2 | 200 mg/kg; 200 ul of 20 mg/ml | 0 (9:00 am) | 1 (10:00 am) | 8 (5:00 pm) |
| Bleed at t = 2 hour | 3 | 200 mg/kg; 200 ul of 20 mg/ml | 0 (9:00 am) | 1 (10:00 am) | 8 (5:00 pm) |
| Bleed at t = 4 hours | 4 | 200 mg/kg; 200 ul of 20 mg/ml | 0, 8 (9:00 am, 5:00 pm) | 2 (11:00 am) | 12 (9:00 pm) |
| Second dose at t = 8 hours | 5 | 200 mg/kg; 200 ul of 20 mg/ml | 0, 8 (9:00 am, 5:00 pm) | 2 (11:00 am) | 12 (9:00 pm) |
| Bleed at t = 8 hours | 6 | 200 mg/kg; 200 ul of 20 mg/ml | 0, 8 (9:00 am, 5:00 pm) | 2 (11:00 am) | 12 (9:00 pm) |
| Bleed at t = 12 hours | 7 | 200 mg/kg; 200 ul of 20 mg/ml | 0, 8 (9:00 am, 5:00 pm) | 4 (1:00) | 24 (9:00 am) |
| Bleed at t = 24 hours | 8 | 200 mg/kg; 200 ul of 20 mg/ml | 0, 8 (9:00 am, 5:00 pm) | 4 (1:00) | 24 (9:00 am) |
|  | 9 | 200 mg/kg; 200 ul of 20 mg/ml | 0, 8 (9:00 am, 5:00 pm) | 4 (1:00) | 24 (9:00 am) |
|  | 10 | 200 mg/kg; 200 ul of 20 mg/ml | 0, 8 (9:00 am, 5:00 pm) | extra | extra |

For each blood sample withdrawn, 50 µL of plasma was isolated for methanol extraction of NZ-331 and NZ-332. These samples were analyzed by liquid chromatography in a Bruker micrOTOF Q-II LC/MS. Samples were quantified using standard calibration curves for NZ-331 and NZ-332 by addition of a known concentration of the compounds to 50 µL of mouse plasma.

Figure 6A:
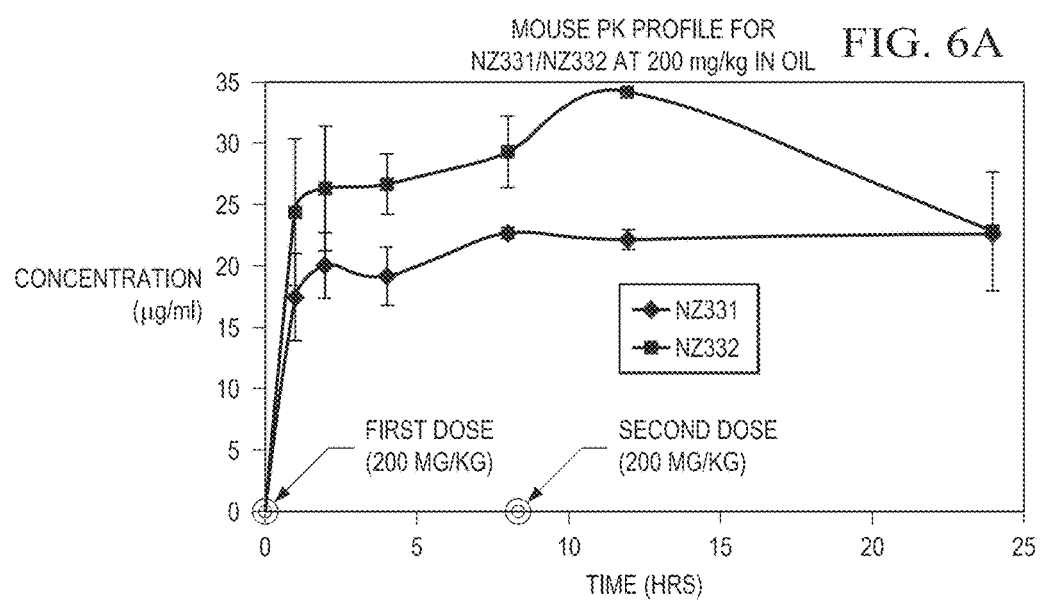
FIG. 6A illustrates the plasma concentration of NZ-331 and NZ-332 in blood samples collected from mice following administration of two doses of NZ-331 and NZ-332 dissolved in canola oil by gavage at a dosage of 200 mg/kg.

FIG. 6A illustrates the plasma concentration of NZ-331 and NZ-332 in blood samples collected from mice following administration of two doses of NZ-331 and NZ-332 dissolved in canola oil by gavage at a dosage of 200 mg/kg. Both NZ-331 and NZ-332 were detected in the samples. The peak plasma concentration of NZ-331 detected was approximately 23 µL/mg in blood samples harvested approximately 12 hours after administration of the first dose by gavage and approximately 4 hours after administration of the second dose by gavage. The peak plasma concentration of NZ-332 detected was approximately 34 µL/mg in blood samples harvested approximately 12 hours after administration of the first dose by gavage and approximately 4 hours after administration of the second dose by gavage.

FIG. 6B illustrates the corrected plasma concentration of NZ-331 in blood samples collected from mice following administration of two doses of NZ-331 and NZ-332 dissolved in canola oil by gavage at a dosage of 200 mg/kg. The peak plasma concentration of NZ-331 detected was approximately 138 µL/mg in blood samples harvested approximately 24 hours after administration of the first dose by gavage and approximately 16 hours after administration of the second dose by gavage.

NZ-313 dissolved in canola oil was administered by gavage to mice at a dosage of 100 mg/kg. Two doses were administered 4 hours apart. Blood was harvested from each mouse at 30 minutes, 90 minutes, and 5 hours after gavage and a final sample was withdrawn from the mice at 4, 8, and 12 hours after gavage. For each blood sample withdrawn, 50 µL of plasma was isolated for methanol extraction of NZ-313. These samples were analyzed by liquid chromatography in a Bruker micrOTOF Q-II LC/MS. Samples were quantified using standard calibration curves for NZ-313 by addition of a known concentration of the compound to 50 µL of mouse plasma.

FIG. 7 illustrates the plasma concentration of NZ-313 in blood samples collected from mice following administration of two doses of NZ-313 dissolved in canola oil by gavage at a dosage of 100 mg/kg. NZ-313 was detected in the samples. The peak plasma concentration of NZ-313 detected was approximately 0.69 µL/mg in blood samples harvested at 30 minutes after gavage.

NZ-313 dissolved in polyethelyne glycol (PEG) was administered by gavage to mice at a dosage of 200 mg/kg. Blood was harvested from each mouse at 30 minutes after gavage and a final sample was withdrawn from the mice at 90 minutes after gavage. For each blood sample withdrawn, 50 µL of plasma was isolated for methanol extraction of NZ-313. These samples were analyzed by liquid chromatography in a Bruker micrOTOF Q-II LC/MS. Samples were quantified using standard calibration curves for NZ-313 by addition of a known concentration of the compound to 50 µL of mouse plasma.

FIG. 8 illustrates the plasma concentration of NZ-313 in blood samples collected from mice following administration of a single dose of NZ-313 dissolved in polyethylene glycol (PEG) by gavage at a dosage of 200 mg/kg. NZ-313 was detected in the samples. The peak plasma concentration of NZ-313 detected was 1 µL/mg in blood samples harvested at 90 minutes after gavage.

FIG. 9 provides a comparison of the plasma concentrations of NZ-313, NZ-313 acid, NZ-313 glucuronidated, NZ331, and NZ-332 in blood samples collected from mice following administration of a single dose of the following compounds by gavage at a dosage of 100 mg/kg: NZ313 dissolved in polyethylene glycol (PEG), NZ-313 acid dissolved in polyethylene glycol (PEG), NZ-313 glucuronidated polyethylene glycol (PEG), NZ-331 dissolved in polyethylene glycol (PEG) or canola oil, or NZ-332 dissolved in polyethylene glycol (PEG) or canola oil.

NZ-3369 dissolved in canola oil was administered by gavage to mice at a dosage of 200 mg/kg. Blood was harvested from each mouse at 1, 2, and 4 hours after gavage and a final sample was withdrawn from the mice at 8 hours after gavage. For each blood sample withdrawn, 50 µL of plasma was isolated for methanol extraction of NZ-369. These samples were analyzed by liquid chromatography in a Bruker micrOTOF Q-II LC/MS. Samples were quantified using standard calibration curves for NZ-369 by addition of a known concentration of the compound to 50 µL of mouse plasma.

Figure 10:
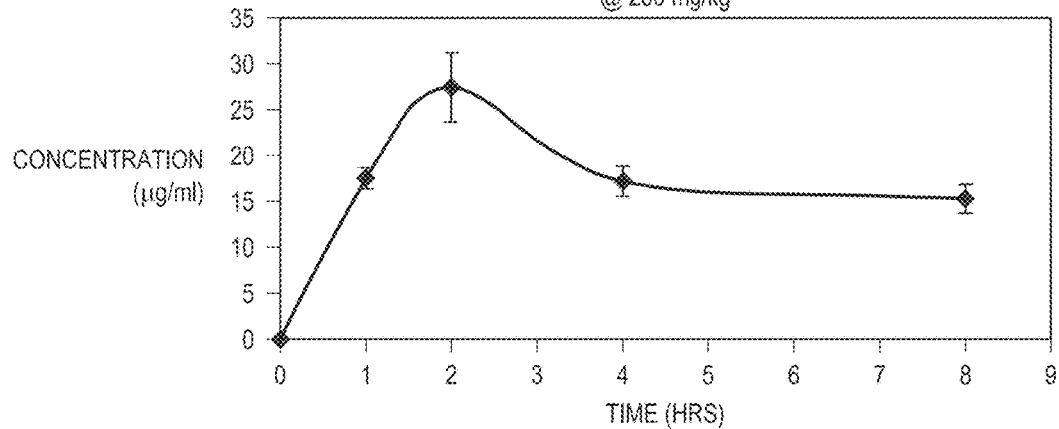
FIG. 10 illustrates the plasma concentration of NZ-369 in blood samples collected from mice following administration of a single dose of NZ-369 dissolved in canola oil by gavage at a dosage of 200 mg/kg.

FIG. 10 illustrates the plasma concentration of NZ-369 in blood samples collected from mice following administration of a single dose of NZ-369 dissolved in canola oil by gavage at a dosage of 200 mg/kg. NZ-313 was detected in the samples. The peak plasma concentration of NZ-369 detected was 27.4 µL/mg in blood samples harvested at 2 hours after gavage.

Figure 11:
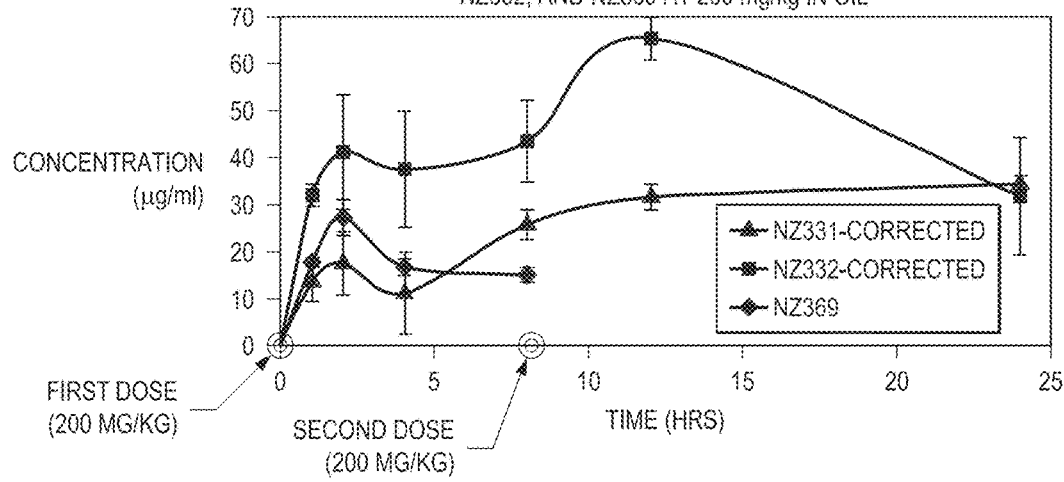
FIG. 11 provides a comparison of the plasma concentrations NZ-331, NZ-332, and NZ-369 in blood samples collected from mice following administration of two doses of NZ-331, NZ-332, and NZ-369 dissolved in canola oil at a dosage of 200 mg/kg 8 hours apart.

FIG. 11 provides a comparison of the plasma concentrations NZ-331, NZ-332, and NZ-369 in blood samples collected from mice following administration of two doses of NZ-331, NZ-332, and NZ-369 dissolved in canola oil at a dosage of 200 mg/kg 8 hours apart. The peak plasma concentration of NZ-331 detected was 34.5 μL/mg in blood samples harvested at 24 hours after gavage. The peak plasma concentration of NZ-332 detected was 65.3.5 μL/mg in blood samples harvested at 12 hours after gavage. The peak plasma concentration of NZ-369 detected was 27.4 μL/mg in blood samples harvested at 2 hours after gavage.

NZ-331, NZ-332, and NZ-369 dissolved in canola oil was administered by gavage to mice once per day for four days at a dosage of 200 mg/kg, 100 mg/kg, and 100 mg/kg, respectively. Blood was harvested from each mouse 24 hours after the first dose and 24 hours after the last dose. Table 5 includes plasma concentration data for these mice.

TABLE 5

Plasma concentration of NZ-331, NZ-332, and NZ-369 following administration of each compound once per day for four days

| Compound | Oral Dose [1 dose/day] × 4 days | Plasma conc. 24 Hrs. after 1st dose | Plasma conc. 24 Hrs. after last dose |
|---|---|---|---|
| NZ-331 | 200 mg/kg | 17.7 (±2.7) μg/ml | 27.1 (±13.7) μg/ml |
| NZ-332 | 100 mg/kg | 2.2 (±0.6) μg/ml | 1.8 (±0.2) μg/ml |
| NZ-369 | 100 mg/kg | 0.74 (±0.09) μg/ml | 0.57 (±0.07) μg/ml |

Additional pharmacokinetic studies of quizalofop-p-ethyl and fenoxaprop-p-ethyl were conducted in rats.

Quizalofop-ethyl was absorbed to a considerable extent by the oral route. Much of what is absorbed is returned to the gastrointestinal tract in bile. Peak blood concentrations occur six to nine hours after exposure, and decline with a half life of round 20 to 30 hours. Quizalofop-ethyl is metabolized to a number of products and distributed to every tissue sampled. Quizalofop-p ethyl converts from ester to acid in ~3 h.

Fenoxaprop-P-ethyl was absorbed rapidly in male and female rats. The test substance was already found in the blood 15 minutes after a single oral administration. The maximum concentration was reached at about 6-8 hours after application. Lowering of the blood concentrations was biphasic with a half-life of 9-11 hours for the initial phase and a half-life of 68-75 hours for the terminal phase. Pharmacokinetic investigation of blood levels revealed practically zero difference between the dose levels of 2 and 10 mg/kg, which were administered as a single dose by oral gavage. The minimum rate of absorption (urinary excretion including cages washes and residues in tissues/organs) was generally higher in females than in males and reached at least 40% of the administered dose.

Example 8—Toxicity Testing

S. cerevisiae cytotoxicity and human fibroblast cytotoxicity testing was performed. The following compounds were not toxic at concentrations at or above 100 μM in both s. cerevisiae cytotoxicity and human fibroblast cytotoxicity testing: NZ-251, NZ-274, NZ-287, NZ-289, NZ-290, NZ-293, NZ-294, NZ-295, NZ-296, NZ-298, NZ-299, NZ-300, NZ-301, NZ-302, NZ-304, NZ-305, NZ-306, NZ-307, NZ-308, NZ-309, NZ-310, NZ-311, NZ-312, NZ-313, NZ-314, NZ-315, NZ-316, NZ-317, NZ-318, NZ-319, NZ-320, NZ-321, NZ-322, NZ-323, NZ-325, NZ-326, NZ-327, NZ-328, NZ-329, NZ-330, NZ-331, NZ-332, NZ-334, NZ-335, NZ-337. NZ-361, NZ-362, NZ-363, NZ-364, NZ-369, NZ-370, NZ-371. NZ-373, NZ-374, NZ-376, NZ-377, NZ-378, NZ-379, NZ-380, NZ-381, NZ-383, NZ-385, NZ-386, NZ-387, NZ-388, NZ-389, NZ-390, NZ-391, NZ-392, NZ-393, NZ-394, NZ-395, NZ-396, NZ-397, NZ-398, NZ-399, NZ-400, NZ-401, NZ-402.

The following compounds were not toxic at concentrations at or above 100 μM in s. cerevisiae cytotoxicity testing: NZ-347, NZ-349, NZ-350, NZ-351, NZ-353, NZ-355, NZ-356, NZ-357, NZ-358, NZ-359, NZ-360, NZ-372.

The following compounds were not toxic at concentrations at or above 100 μM in human fibroblast cytotoxicity testing: NZ-303, NZ-338, NZ-341, NZ-342, NZ-343, NZ-345, NZ-346, NZ-368, NZ-365, NZ-382, fenoxaprop-p, fenoxaprop-p-ethyl.

The following compounds were not toxic at concentrations at or above 25 μM and at or below 50 μM in s. cerevisiae cytotoxicity testing: NZ-348, NZ-352, NZ-366, NZ-368.

The following compound was not toxic at concentrations at or above 25 μM and at or below 50 μM in human fibroblast cytotoxicity testing: NZ-366.

The following compounds were not toxic at concentrations at or above 50 μM and at or below 100 μM in s. cerevisiae cytotoxicity testing: NZ-336, NZ-354, NZ-365, NZ-382.

The following compound was not toxic at concentrations at or above 50 μM and at or below 100 μM in human fibroblast cytotoxicity testing: NZ-336.

Example 9—Synthesis of Aryloxyphenoxyacetate Derivatives

Aryloxyphenoxyacetate derivatives can be prepared according the following scheme:

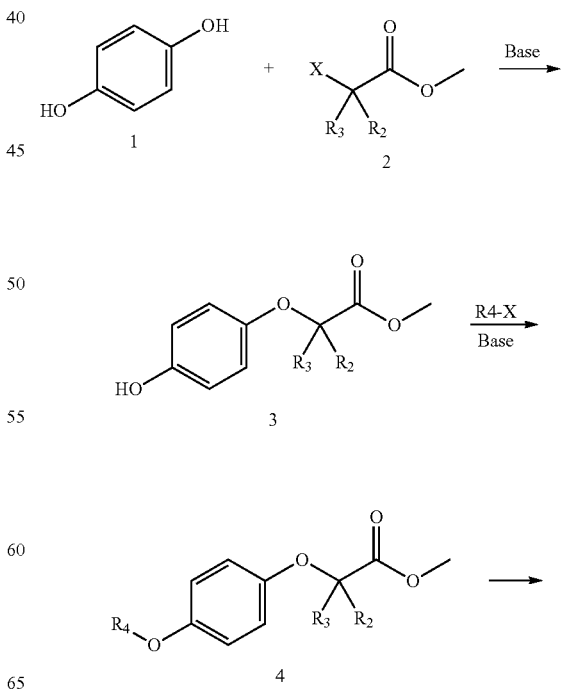

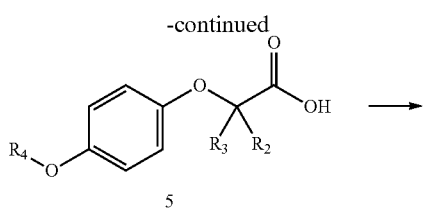

The compounds (3) are synthesized by condensation of hydroquinone (1) with chloro- or bromo-substituted acetate (2) at a temperature range from 5° C. to 120° C. in water, or organic solvent, such as DMF, DMSO, ethanol, in the presence of base, such as NaOH, K$_2$CO$_3$, or NaH. Substitution of compounds (3) with aromatic chloride or bromide (R4-X) in organic solvent, such as DMF, DMSO, dioxane, acetonitril, ethanol in the presence or absence of a catalyst, such as CuI, at a temperature range from 25° C. to 150° C. in the presence of base, such as K$_2$CO$_3$. Li$_2$CO$_3$, LiOH, KOH, produces ester (4). Hydrolysis of ester (4) will give acid (5). Coupling of acid (5) with amine in the presence of coupling reagents, such as EDCI, CDI or via acyl chloride in organic solvent, such as DCM, THF, DMF, produces amide (6).

Other aryloxyphenoxy or aryloxyphenyl-acetate, -acetyl amide, -acyl sulfonamide can be prepared by similar methods. It is apparent to one skilled in art that other sequence of the reaction, and alternative reagents can be used for the synthesis of compounds of the present disclosure. These alternatives for the synthesis of the derivatives are within the scope of this invention.

Although only exemplary embodiments of the invention are specifically described above, it will be appreciated that modifications and variations of these examples are possible without departing from the spirit and intended scope of the invention. For example, various specific formulations including components not listed herein and specific methods of administering such formulations may be developed using the ordinary skill in the art. Numeric amounts expressed herein will be understood by one of ordinary skill in the art to include amounts that are approximately or about those expressed. Furthermore, the term "or" as used herein is not intended to express exclusive options (either/or) unless the context specifically indicates that exclusivity is required; rather "or" is intended to be inclusive (and/or).

The invention claimed is:

1. A composition comprising:
   a drug comprising 2-{4-[(6-chloro-1,3-benzothiazol-2-yl)oxy]phenyl}-N-methylpropanamide, 1-{4-[(6-chloro-1,3-benzothiazol-2-yl)oxy]phenyl}-3-(propan-2-yl)urea, 1-{4-[(6-fluoro-1,3-benzothiazol-2-yl)oxy]phenyl}-3-(propan-2-yl)urea, or 2-{4-[(6-chloro-1,3-benzothiazol-2-yl)oxy]phenyl}-N-methoxypropanamide, or a pharmaceutically acceptable salt, hydrate, or prodrug thereof in an amount and formulation sufficient to inhibit a *mycobacterium* expressing Acetyl-CoA carboxyltransferase β-subunit D6 (AccD6); and
   a pharmaceutically acceptable carrier.

2. The composition of claim 1, further comprising a salt, a buffer, a preservative, or a solubility enhancer.

3. The composition of claim 1, wherein the *mycobacterium* is *Mycobacterium tuberculosis* or *Mycobacterium bovis*.

4. A method of inhibiting a *mycobacterium* expressing Acetyl-CoA carboxyltransferase β-subunit D6 (AccD6) comprising:
   administering a composition comprising a drug, having the formula:

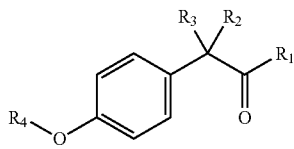

wherein:
   $R_1$ is selected from —OH, —OCH$_3$, —NHOCH$_3$, —NHCH$_3$, and —NHCH(CH$_3$)$_2$ groups;
   $R_2$ and $R_3$ are both H or at least one of $R_2$ and $R_3$ is —CH$_3$; and
   $R_4$ is selected from a 1,3-benzothiazole-2-yl, 1,3-benzothiazole-2-yl substituted with a halogen or —OCH$_3$ group, and quinoxaline-2-yl, or a pharmaceutically acceptable salt, hydrate, or prodrug thereof to the *mycobacterium* in an amount and for a time sufficient to inhibit AccD6 in the *mycobacterium*.

5. The method of claim 4, wherein the *mycobacterium* is pathogenic.

6. The method of claim 4, wherein the *mycobacterium* is selected from the group consisting of *Mycobacterium tuberculosis* or *Mycobacterium bovis*.

7. The method of claim 4, wherein the composition is substantially nontoxic to animals.

8. The method of claim 4, wherein the *mycobacterium* is drug resistant.

9. The method of claim 4, wherein the *mycobacterium* is multi-drug resistant.

10. The method of claim 4, wherein the drug has a minimum inhibitory concentration for the *mycobacterium* of between 0.1 μM and 50 μM.

11. The method of claim 4, wherein $R_1$ is selected from —OH, —OMe, —NHOCH$_3$, —NHCH$_3$, and —NHCH(CH$_3$)$_2$ groups;
    $R_2$ and $R_3$ are both H or one of $R_2$ and $R_3$ is —CH$_3$; and
    $R_4$ is 1,3-benzothiazole-2-yl.

12. The method of claim 4, wherein the drug is 2-{4-[(6-chloro-1,3-benzothiazol-2-yl)oxy]phenyl}-N-methylpropanamide, 1-{4-[(6-chloro-1,3-benzothiazol-2-yl)oxy]phenyl}-3-(propan-2-yl)urea, 1-{4-[(6-fluoro-1,3-benzothiazol-2-yl)oxy]phenyl}-3-(propan-2-yl)urea, or 2-{4-[(6-chloro-1,3-benzothiazol-2-yl)oxy]phenyl}-N-methoxypropanamide.

13. The method of claim 4, wherein the drug has a minimum inhibitory concentration for the *mycobacterium* of between 0.3 μM and 20 μM.

14. The method of claim 4, wherein the drug has a minimum inhibitory concentration for the *mycobacterium* of between 1 μM and 10 μM.

15. The method of claim 4, wherein the drug has a minimum inhibitory concentration for the *mycobacterium* of between 1 μM and 25 μM.

16. The method of claim 4, wherein the drug has a unit dosage of between 1 mg/kg body weight and 500 mg/kg body weight.

17. The method of claim 4, wherein the drug has a unit dosage of between 5 mg/kg body weight to about 350 mg/kg body weight.

18. The method of claim 4, wherein the drug has a unit dosage of between 0 mg/kg body weight and about 200 mg/kg body weight.

* * * * *

SEQUENCE LISTING

```
<160> NUMBER OF SEQ ID NOS: 2

<210> SEQ ID NO 1
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 1
agatgaagcc atatgacaat catggccccc gaggcggttg                         40

<210> SEQ ID NO 2
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 2
agagtaagct tacagcggga tgttcttgag gcggcc                             36
```